(12) United States Patent
Eskridge et al.

(10) Patent No.: US 9,510,835 B2
(45) Date of Patent: Dec. 6, 2016

(54) METHODS AND SYSTEMS FOR ENDOVASCULARLY CLIPPING AND REPAIRING LUMEN AND TISSUE DEFECTS

(71) Applicant: Pulsar Vascular, Inc., San Jose, CA (US)

(72) Inventors: Joseph Eskridge, Clyde Hill, WA (US); Gilbert Clarke, Seattle, WA (US); Matthew Pease, Mountain View, CA (US); Gregory Martin Mast, Freemont, CA (US); John Conrad Muskivitch, Cupertino, CA (US)

(73) Assignee: Pulsar Vascular, Inc., Los Gatos, CA (US)

( * ) Notice: Subject to any disclaimer, the term of this patent is extended or adjusted under 35 U.S.C. 154(b) by 0 days.

(21) Appl. No.: 14/022,088

(22) Filed: Sep. 9, 2013

(65) Prior Publication Data

US 2014/0142608 A1    May 22, 2014

Related U.S. Application Data

(63) Continuation of application No. 11/737,700, filed on Apr. 19, 2007, now Pat. No. 8,551,132, which is a (Continued)

(51) Int. Cl.
*A61M 29/00* (2006.01)
*A61B 17/122* (2006.01)
(Continued)

(52) U.S. Cl.
CPC ....... *A61B 17/122* (2013.01); *A61B 17/12022* (2013.01); *A61B 17/12113* (2013.01); (Continued)

(58) Field of Classification Search
CPC ................... A61B 17/12109; A61B 17/12113
(Continued)

(56) References Cited

U.S. PATENT DOCUMENTS

| 3,868,956 | A | 3/1975 | Alfidi et al. |
| 4,164,045 | A | 8/1979 | Bokros et al. |

(Continued)

FOREIGN PATENT DOCUMENTS

| CN | 1384726 | 12/2002 |
| CN | 1399530 | 2/2003 |

(Continued)

OTHER PUBLICATIONS

Polytetraflouroethylene Implants, DermNet NZ, Nov. 11, 2005, http://dermetnz.org/polytetrafluoroethylene.html.
(Continued)

*Primary Examiner* — Diane Yabut
(74) *Attorney, Agent, or Firm* — Perkins Coie LLP

(57) ABSTRACT

An implantable closure structure is delivered using minimally invasive techniques, and inhibits the migration of liquid and particulate matter from inside a physiological cavity or opening, such as an aneurysm or a septal defect, as well as inhibiting the flow of liquid and particulate matter, such as from an associated blood vessel or chamber, into the physiological cavity or opening. The device has a closure structure that covers the neck or opening of a cavity and has one or more anchoring structures for supporting and retaining the closure structure in place across the cavity or opening.

29 Claims, 9 Drawing Sheets

Related U.S. Application Data continuation-in-part of application No. 11/324,827, filed on Jan. 3, 2006, now Pat. No. 8,545,530, said application No. 11/737,700 is a continuation-in-part of application No. PCT/US2006/040907, filed on Oct. 18, 2006.

(60) Provisional application No. 60/728,052, filed on Oct. 19, 2005, provisional application No. 60/803,200, filed on May 25, 2006, provisional application No. 60/747,400, filed on May 16, 2006, provisional application No. 60/728,052, filed on Oct. 19, 2005, provisional application No. 60/823,730, filed on Aug. 28, 2006.

(51) Int. Cl.
    *A61B 17/12*    (2006.01)
    *A61B 17/00*    (2006.01)

(52) U.S. Cl.
    CPC .. *A61B 17/12172* (2013.01); *A61B 17/12109* (2013.01); *A61B 90/39* (2016.02); *A61B 2017/00867* (2013.01); *A61B 2017/1205* (2013.01); *A61B 2017/12054* (2013.01)

(58) Field of Classification Search
    USPC .................................. 606/191, 200; 623/1.11
    See application file for complete search history.

(56) References Cited

U.S. PATENT DOCUMENTS

| | | |
|---|---|---|
| 4,248,234 A | 2/1981 | Assenza et al. |
| 4,645,495 A | 2/1987 | Vaillancourt |
| 4,651,751 A | 3/1987 | Swendson et al. |
| 4,665,906 A | 5/1987 | Jervis |
| 4,706,671 A | 11/1987 | Weinrib |
| 4,710,192 A | 12/1987 | Liotta et al. |
| 4,739,768 A | 4/1988 | Engelson |
| 4,820,298 A | 4/1989 | Leveen et al. |
| 4,873,978 A | 10/1989 | Ginsburg |
| 4,909,787 A | 3/1990 | Danforth |
| 4,994,069 A | 2/1991 | Ritchart et al. |
| 5,011,488 A | 4/1991 | Ginsburg |
| 5,074,869 A | 12/1991 | Daicoff |
| 5,122,136 A | 6/1992 | Guglielmi et al. |
| 5,226,911 A | 7/1993 | Chee et al. |
| 5,250,071 A | 10/1993 | Palermo |
| 5,261,916 A | 11/1993 | Engelson |
| 5,263,964 A | 11/1993 | Purdy |
| 5,263,974 A | 11/1993 | Matsutani et al. |
| 5,271,414 A | 12/1993 | Partika et al. |
| 5,304,195 A | 4/1994 | Twyford, Jr. et al. |
| 5,334,168 A | 8/1994 | Hemmer |
| 5,342,386 A | 8/1994 | Trotta |
| 5,350,397 A | 9/1994 | Palermo et al. |
| 5,354,295 A | 10/1994 | Guglielmi et al. |
| 5,527,338 A | 6/1996 | Purdy |
| 5,531,685 A | 7/1996 | Hemmer et al. |
| 5,578,074 A | 11/1996 | Mirigian |
| 5,624,449 A | 4/1997 | Pham et al. |
| 5,643,254 A | 7/1997 | Scheldrup et al. |
| 5,665,106 A | 9/1997 | Hammerslag |
| 5,669,931 A | 9/1997 | Kupiecki et al. |
| 5,693,067 A | 12/1997 | Purdy |
| 5,733,294 A | 3/1998 | Forber et al. |
| 5,733,329 A | 3/1998 | Wallace et al. |
| 5,749,890 A | 5/1998 | Shaknovich |
| 5,749,894 A | 5/1998 | Engelson |
| 5,759,194 A | 6/1998 | Hammerslag |
| 5,766,192 A | 6/1998 | Zacca |
| 5,769,884 A | 6/1998 | Solovay |
| 5,797,953 A | 8/1998 | Tekulve |
| 5,814,062 A | 9/1998 | Sepetka et al. |
| 5,843,103 A | 12/1998 | Wulfman |
| D407,818 S | 4/1999 | Mariant et al. |
| 5,895,391 A | 4/1999 | Farnholtz |
| 5,895,410 A | 4/1999 | Forber et al. |
| 5,910,145 A | 6/1999 | Fischell et al. |
| 5,911,737 A | 6/1999 | Lee et al. |
| 5,916,235 A | 6/1999 | Guglielmi |
| 5,925,060 A | 7/1999 | Forber |
| 5,925,062 A | 7/1999 | Purdy |
| 5,925,683 A | 7/1999 | Park |
| 5,928,260 A | 7/1999 | Chin et al. |
| 5,933,329 A | 8/1999 | Tijanoc et al. |
| 5,935,114 A | 8/1999 | Jang et al. |
| 5,935,148 A | 8/1999 | Villar et al. |
| 5,951,599 A | 9/1999 | McCrory |
| 5,968,068 A | 10/1999 | Dehdashtian et al. |
| 5,980,514 A | 11/1999 | Kupiecki et al. |
| 5,980,554 A | 11/1999 | Lenker et al. |
| 5,984,944 A | 11/1999 | Forber |
| 6,007,544 A | 12/1999 | Kim |
| 6,013,055 A | 1/2000 | Bampos et al. |
| 6,022,341 A | 2/2000 | Lentz |
| 6,036,720 A * | 3/2000 | Abrams et al. .............. 606/213 |
| 6,063,070 A | 5/2000 | Eder |
| 6,063,104 A | 5/2000 | Villar et al. |
| 6,071,263 A | 6/2000 | Kirkman |
| 6,077,291 A | 6/2000 | Das |
| 6,081,263 A | 6/2000 | LeGall et al. |
| 6,090,125 A | 7/2000 | Horton |
| 6,093,199 A | 7/2000 | Brown et al. |
| 6,096,021 A | 8/2000 | Helm et al. |
| 6,096,034 A | 8/2000 | Kupiecki et al. |
| 6,102,917 A | 8/2000 | Maitland et al. |
| 6,110,191 A | 8/2000 | Dehdashtian et al. |
| 6,117,157 A | 9/2000 | Tekulve |
| 6,139,564 A | 10/2000 | Teoh |
| 6,146,339 A | 11/2000 | Biagtan et al. |
| 6,152,944 A | 11/2000 | Holman et al. |
| 6,168,615 B1 * | 1/2001 | Ken et al. ..................... 623/1.1 |
| 6,168,622 B1 | 1/2001 | Mazzocchi |
| 6,174,322 B1 | 1/2001 | Schneidt |
| 6,183,495 B1 | 2/2001 | Lenker et al. |
| 6,193,708 B1 | 2/2001 | Ken et al. |
| RE37,117 E | 3/2001 | Palermo |
| 6,221,066 B1 | 4/2001 | Ferrera et al. |
| 6,221,086 B1 | 4/2001 | Forber |
| 6,224,610 B1 | 5/2001 | Ferrera |
| 6,228,052 B1 | 5/2001 | Pohndorf |
| 6,261,305 B1 | 7/2001 | Marotta et al. |
| 6,293,960 B1 | 9/2001 | Ken |
| 6,296,622 B1 | 10/2001 | Kurz et al. |
| 6,309,367 B1 | 10/2001 | Boock |
| 6,325,807 B1 | 12/2001 | Que |
| 6,344,041 B1 | 2/2002 | Kupiecki et al. |
| 6,344,048 B1 | 2/2002 | Chin et al. |
| 6,361,558 B1 | 3/2002 | Hieshima et al. |
| 6,375,668 B1 | 4/2002 | Gifford et al. |
| 6,383,174 B1 | 5/2002 | Eder |
| 6,398,791 B1 | 6/2002 | Que et al. |
| 6,478,773 B1 | 11/2002 | Gandhi et al. |
| 6,491,711 B1 | 12/2002 | Durcan |
| 6,517,515 B1 | 2/2003 | Eidenschink |
| 6,530,935 B2 | 3/2003 | Wensel et al. |
| 6,533,905 B2 | 3/2003 | Johnson et al. |
| 6,554,794 B1 | 4/2003 | Mueller et al. |
| 6,589,256 B2 | 7/2003 | Forber |
| 6,592,605 B2 | 7/2003 | Lenker et al. |
| 6,613,074 B1 * | 9/2003 | Mitelberg et al. ........... 623/1.11 |
| 6,616,681 B2 | 9/2003 | Hanson et al. |
| 6,626,889 B1 | 9/2003 | Simpson et al. |
| 6,626,928 B1 | 9/2003 | Raymond et al. |
| 6,638,268 B2 | 10/2003 | Niazi |
| 6,652,556 B1 * | 11/2003 | VanTassel et al. ........... 606/200 |
| 6,663,607 B2 | 12/2003 | Slaikeu et al. |
| 6,663,648 B1 | 12/2003 | Trotta |
| 6,669,795 B2 | 12/2003 | Johnson et al. |
| 6,672,338 B1 | 1/2004 | Esashi et al. |
| 6,679,836 B2 | 1/2004 | Couvillon, Jr. |
| 6,679,903 B2 | 1/2004 | Kurz |

(56) References Cited

U.S. PATENT DOCUMENTS

| | | |
|---|---|---|
| 6,689,141 B2 | 2/2004 | Ferrera et al. |
| 6,694,979 B2 | 2/2004 | Deem et al. |
| 6,723,112 B2 | 4/2004 | Ho et al. |
| 6,740,073 B1 | 5/2004 | Saville |
| 6,740,277 B2 | 5/2004 | Howell et al. |
| 6,746,468 B1 | 6/2004 | Sepetka et al. |
| 6,780,196 B2 | 8/2004 | Chin et al. |
| 6,790,218 B2 | 9/2004 | Jayaraman |
| 6,802,851 B2 | 10/2004 | Jones et al. |
| 6,811,560 B2 | 11/2004 | Jones et al. |
| 6,824,553 B1 | 11/2004 | Samson et al. |
| 6,835,185 B2 | 12/2004 | Ramzipoor et al. |
| 6,837,870 B2 | 1/2005 | Duchamp |
| 6,843,802 B1 | 1/2005 | Villalobos et al. |
| 6,855,153 B2 | 2/2005 | Saadat |
| 6,863,678 B2 | 3/2005 | Lee et al. |
| 6,890,218 B2 | 5/2005 | Patwardhan et al. |
| 6,911,037 B2 | 6/2005 | Gainor et al. |
| 6,936,055 B1 | 8/2005 | Ken et al. |
| 6,939,055 B2 | 9/2005 | Durrant et al. |
| 6,986,774 B2 | 1/2006 | Middleman et al. |
| 6,994,092 B2 | 2/2006 | van der Burg et al. |
| 7,011,094 B2 | 3/2006 | Rapacki et al. |
| 7,033,374 B2 | 4/2006 | Schaefer et al. |
| 7,033,387 B2 | 4/2006 | Zadno-Azizi et al. |
| 7,122,043 B2 | 10/2006 | Greenhalgh et al. |
| 7,147,659 B2 | 12/2006 | Jones |
| 7,156,871 B2 | 1/2007 | Jones et al. |
| 7,169,177 B2 | 1/2007 | Obara |
| 7,229,461 B2 | 6/2007 | Chin et al. |
| 7,232,461 B2 | 6/2007 | Ramer |
| 7,267,679 B2 | 9/2007 | McGuckin, Jr. et al. |
| 7,306,622 B2 | 12/2007 | Jones et al. |
| 7,322,960 B2 | 1/2008 | Yamamoto et al. |
| 7,343,856 B2 | 3/2008 | Blohdorn |
| 7,387,629 B2 | 6/2008 | Vanney et al. |
| 7,410,482 B2 | 8/2008 | Murphy et al. |
| 7,569,066 B2 | 8/2009 | Gerberding et al. |
| 7,608,088 B2 | 10/2009 | Jones et al. |
| 7,662,168 B2 | 2/2010 | McGuckin, Jr. et al. |
| 7,857,825 B2 | 12/2010 | Moran et al. |
| 7,892,254 B2 | 2/2011 | Klint et al. |
| 8,016,853 B2 | 9/2011 | Griffen et al. |
| 8,075,585 B2 | 12/2011 | Lee et al. |
| 8,187,315 B1 | 5/2012 | Clauson et al. |
| 8,262,692 B2 | 9/2012 | Rudakov |
| 8,388,650 B2 | 3/2013 | Gerberding et al. |
| 8,444,667 B2 | 5/2013 | Porter |
| 8,470,013 B2 | 6/2013 | Duggal et al. |
| 8,540,763 B2 | 9/2013 | Jones et al. |
| 8,545,530 B2 | 10/2013 | Eskridge et al. |
| 8,551,132 B2 | 10/2013 | Eskridge et al. |
| 8,556,953 B2 | 10/2013 | Berez et al. |
| 8,715,312 B2 | 5/2014 | Burke et al. |
| 8,715,338 B2 | 5/2014 | Frid |
| 8,728,141 B2 | 5/2014 | Riina et al. |
| 8,747,430 B2 | 6/2014 | Porter |
| 8,771,341 B2 | 7/2014 | Strauss et al. |
| 8,915,950 B2 | 12/2014 | Cam et al. |
| 8,926,680 B2 | 1/2015 | Ferrera et al. |
| 8,956,399 B2 | 2/2015 | Cam et al. |
| 8,979,893 B2 | 3/2015 | Gerberding et al. |
| 9,060,886 B2 | 6/2015 | Molaei et al. |
| 9,107,670 B2 | 8/2015 | Hannes et al. |
| 9,119,625 B2 | 9/2015 | Bachman et al. |
| 9,179,918 B2 | 11/2015 | Levy et al. |
| 9,186,267 B2 | 11/2015 | Losordo et al. |
| 9,192,388 B2 | 11/2015 | Cam et al. |
| 9,211,124 B2 | 12/2015 | Campbell et al. |
| 9,259,229 B2 | 2/2016 | Abrams et al. |
| 9,277,924 B2 | 3/2016 | Clarke et al. |
| 2002/0026232 A1 | 2/2002 | Marotta et al. |
| 2003/0033003 A1 | 2/2003 | Harrison et al. |
| 2003/0057156 A1* | 3/2003 | Peterson et al. ............ 210/645 |
| 2003/0139802 A1 | 7/2003 | Wulfman et al. |
| 2003/0181922 A1 | 9/2003 | Alferness |
| 2003/0181942 A1* | 9/2003 | Sutton et al. ................. 606/200 |
| 2003/0195385 A1 | 10/2003 | DeVore |
| 2003/0195553 A1 | 10/2003 | Wallace et al. |
| 2003/0212412 A1 | 11/2003 | Dillard et al. |
| 2004/0044391 A1 | 3/2004 | Porter |
| 2004/0068314 A1 | 4/2004 | Jones et al. |
| 2004/0087998 A1 | 5/2004 | Lee et al. |
| 2004/0111112 A1 | 6/2004 | Hoffmann |
| 2004/0158311 A1 | 8/2004 | Berhow et al. |
| 2004/0167597 A1 | 8/2004 | Costantino et al. |
| 2004/0167602 A1 | 8/2004 | Fischell et al. |
| 2004/0172056 A1 | 9/2004 | Guterman et al. |
| 2004/0193246 A1 | 9/2004 | Ferrera |
| 2004/0210248 A1 | 10/2004 | Gordon et al. |
| 2004/0210298 A1 | 10/2004 | Rabkin et al. |
| 2005/0021023 A1 | 1/2005 | Guglielmi et al. |
| 2005/0025797 A1 | 2/2005 | Wang et al. |
| 2005/0033349 A1 | 2/2005 | Jones et al. |
| 2005/0033409 A1 | 2/2005 | Burke et al. |
| 2005/0096728 A1 | 5/2005 | Ramer |
| 2005/0177224 A1 | 8/2005 | Fogarty et al. |
| 2006/0004436 A1 | 1/2006 | Amarant et al. |
| 2006/0030929 A1 | 2/2006 | Musbach |
| 2006/0052862 A1 | 3/2006 | Kanamaru et al. |
| 2006/0058837 A1 | 3/2006 | Bose et al. |
| 2006/0064151 A1 | 3/2006 | Guterman et al. |
| 2006/0106418 A1 | 5/2006 | Seibold et al. |
| 2006/0200234 A1 | 9/2006 | Hines |
| 2006/0206199 A1 | 9/2006 | Churchwell et al. |
| 2006/0247680 A1* | 11/2006 | Amplatz et al. ............ 606/213 |
| 2006/0259131 A1 | 11/2006 | Molaei et al. |
| 2006/0264905 A1 | 11/2006 | Eskridge et al. |
| 2006/0264907 A1 | 11/2006 | Eskridge et al. |
| 2007/0067015 A1 | 3/2007 | Jones et al. |
| 2007/0088387 A1 | 4/2007 | Eskridge et al. |
| 2007/0106311 A1 | 5/2007 | Wallace et al. |
| 2007/0191884 A1 | 8/2007 | Eskridge et al. |
| 2007/0198075 A1 | 8/2007 | Levy |
| 2007/0203567 A1 | 8/2007 | Levy |
| 2007/0270902 A1 | 11/2007 | Slazas et al. |
| 2008/0004653 A1 | 1/2008 | Sherman et al. |
| 2008/0004692 A1 | 1/2008 | Henson et al. |
| 2008/0039930 A1 | 2/2008 | Jones et al. |
| 2008/0147100 A1 | 6/2008 | Wallace |
| 2008/0183143 A1 | 7/2008 | Palisis et al. |
| 2008/0221600 A1 | 9/2008 | Dieck et al. |
| 2008/0269774 A1 | 10/2008 | Garcia et al. |
| 2008/0319533 A1 | 12/2008 | Lehe |
| 2009/0069880 A1 | 3/2009 | Vonderwalde et al. |
| 2009/0125053 A1 | 5/2009 | Ferrera et al. |
| 2009/0306678 A1 | 12/2009 | Hardert et al. |
| 2010/0023105 A1 | 1/2010 | Levy et al. |
| 2010/0063531 A1 | 3/2010 | Rudakov et al. |
| 2010/0094335 A1 | 4/2010 | Gerberding et al. |
| 2011/0022149 A1 | 1/2011 | Cox et al. |
| 2011/0270373 A1 | 11/2011 | Sampognaro et al. |
| 2012/0143237 A1 | 6/2012 | Cam et al. |
| 2012/0143317 A1 | 6/2012 | Cam et al. |
| 2012/0245674 A1 | 9/2012 | Molaei et al. |
| 2012/0290067 A1 | 11/2012 | Cam et al. |
| 2012/0296361 A1 | 11/2012 | Cam et al. |
| 2013/0090682 A1 | 4/2013 | Bachman et al. |
| 2013/0204290 A1 | 8/2013 | Clarke et al. |
| 2013/0268046 A1 | 10/2013 | Gerberding et al. |
| 2013/0268053 A1 | 10/2013 | Molaei et al. |
| 2013/0274862 A1 | 10/2013 | Cox et al. |
| 2013/0274863 A1 | 10/2013 | Cox et al. |
| 2013/0274866 A1 | 10/2013 | Cox et al. |
| 2013/0274868 A1 | 10/2013 | Cox et al. |
| 2013/0304109 A1 | 11/2013 | Abrams et al. |
| 2014/0052233 A1 | 2/2014 | Cox et al. |
| 2014/0058420 A1 | 2/2014 | Hannes et al. |
| 2014/0121752 A1 | 5/2014 | Losordo et al. |
| 2014/0128901 A1 | 5/2014 | Kang et al. |
| 2014/0180377 A1 | 6/2014 | Bose et al. |
| 2014/0236216 A1 | 8/2014 | Gerberding |
| 2015/0039015 A1 | 2/2015 | Gerberding |
| 2015/0142025 A1 | 5/2015 | Brandeis |

(56) References Cited

U.S. PATENT DOCUMENTS

| | | |
|---|---|---|
| 2015/0142042 A1 | 5/2015 | Cox |
| 2015/0142043 A1 | 5/2015 | Furey |
| 2015/0157329 A1 | 6/2015 | Rudakov et al. |
| 2015/0157331 A1 | 6/2015 | Levy et al. |
| 2015/0164512 A1 | 6/2015 | Chin et al. |
| 2015/0164665 A1 | 6/2015 | Cam et al. |
| 2015/0182361 A1 | 7/2015 | Ferrera et al. |
| 2015/0196305 A1 | 7/2015 | Meyer et al. |
| 2015/0216534 A1 | 8/2015 | Riina et al. |
| 2015/0216687 A1 | 8/2015 | Gerberding et al. |
| 2015/0245932 A1 | 9/2015 | Molaei et al. |
| 2015/0250628 A1 | 9/2015 | Monstadt et al. |
| 2015/0282962 A1 | 10/2015 | Strauss et al. |
| 2015/0327867 A1 | 11/2015 | Bachman et al. |
| 2015/0342612 A1 | 12/2015 | Wu et al. |
| 2016/0015395 A1 | 1/2016 | Molaei et al. |
| 2016/0015396 A1 | 1/2016 | Cox et al. |
| 2016/0030050 A1 | 2/2016 | Franano et al. |
| 2016/0038153 A1 | 2/2016 | Losordo et al. |
| 2016/0249936 A1 | 9/2016 | Clarke et al. |

FOREIGN PATENT DOCUMENTS

| | | |
|---|---|---|
| CN | 1399531 A | 2/2003 |
| DE | 102008028308 | 4/2009 |
| EP | 0820726 | 1/1998 |
| EP | 00996372 | 5/2000 |
| EP | 1269935 | 1/2003 |
| EP | 1527753 A2 | 5/2005 |
| JP | 2001286478 | 10/2001 |
| JP | 2002516705 A | 6/2002 |
| JP | 2003512129 A | 4/2003 |
| JP | 2005522266 A | 7/2005 |
| WO | WO-9724978 | 7/1997 |
| WO | WO-9726939 | 7/1997 |
| WO | WO-9731672 | 9/1997 |
| WO | WO-9823227 | 6/1998 |
| WO | WO-9850102 A1 | 11/1998 |
| WO | WO-9905977 | 2/1999 |
| WO | WO-9907294 | 2/1999 |
| WO | WO-9915225 | 4/1999 |
| WO | WO-0013593 | 3/2000 |
| WO | WO-0130266 | 5/2001 |
| WO | WO-2001093782 | 12/2001 |
| WO | WO-2002000139 | 1/2002 |
| WO | WO-0213899 | 2/2002 |
| WO | WO-02071977 | 9/2002 |
| WO | WO-02078777 | 10/2002 |
| WO | WO-02087690 | 11/2002 |
| WO | WO-03059176 | 7/2003 |
| WO | WO-03075793 A1 | 9/2003 |
| WO | WO-2004019790 | 3/2004 |
| WO | WO-2004026149 | 4/2004 |
| WO | WO-2004105599 | 12/2004 |
| WO | WO-05033409 A1 | 4/2005 |
| WO | WO-2005082279 | 9/2005 |
| WO | WO-2007/047851 | 4/2007 |
| WO | WO-2008/151204 | 12/2008 |
| WO | WO-2010/028314 | 3/2010 |
| WO | WO-2011029063 | 3/2011 |
| WO | WO-2014029835 A1 | 2/2014 |
| WO | WO-2015179377 A1 | 11/2015 |

OTHER PUBLICATIONS

International Search Report for International Application No. PCT/US06/40907, Mail Date May 1, 2008, 2 pages.

Extended European Search Report, European Application No. 06826291.4, Nov. 19, 2009, 7 pages.

Singapore Examination Report for Singapore Application No. 200802811-0, Mail Date Jul. 12, 2009, 7 pages.

International Search Report and Written Opinion for International Application No. PCT/US2009/056133, Mail Date Oct. 26, 2009, 11 pages.

MICRUS COPR.; "Concourse 14 Microcatheter" Product Brochure; Sunnyvale, CA, USA.

Cordis NeuroVascular, Inc.; "Masstransit Microcatheter," Product Brochure; No. 153-8383-3; Miami Lakes, FL, USA (2003).

Cordis NeuroVascular, Inc.; "Prowler Select Plus Microcatheter," Product Brochure; No. 154-9877-1; Miami Lakes, FL, USA (2003).

Cordis NeuroVascular, Inc.; "Rapid Transit Microcatheter," Product Brochure; No. 152-7369-2; Miami Lakes, FL, USA (2003).

Cordis NeuroVascular, Inc.; "Prowler Select LP Microcatheter," Product Brochure; No. 155-5585; Miami Lakes, FL, USA (2004).

Gupta et al. SMST-2003: Proc. Intl. Conf. Shape Memory Superelastic Technol.; Pacific Grove, CA; p. 639; 2003.

International Search Report and Written Opinion for Application No. PCT/US2010/047908, Mail Date May 25, 2011.

International Search Report and Written Opinion for International Application No. PCT/US2010/047908, mailing date Mar. 15, 2012, 11 pages.

International Search Report and Written Opinion for International Application No. PCT/US2012/040552, mailing date Aug. 28, 2012, 14 pages.

International Search Report and Written Opinion for International Application PCT/US2012/040536, mailing date Oct. 15, 2012, 17 pages.

International Search Report and Written Opinion for International Application PCT/US2012/040558, mailing date Oct. 8, 2012, 17 pages.

International Search Report and Written Opinion for International Application PCT/US2012/059133, mailing date Mar. 11, 2013, 15 pages.

International Search Report and Written Opinion for International Application PCT/US2013/031793, mailing date Jun. 26, 2013, 14 pages.

\* cited by examiner

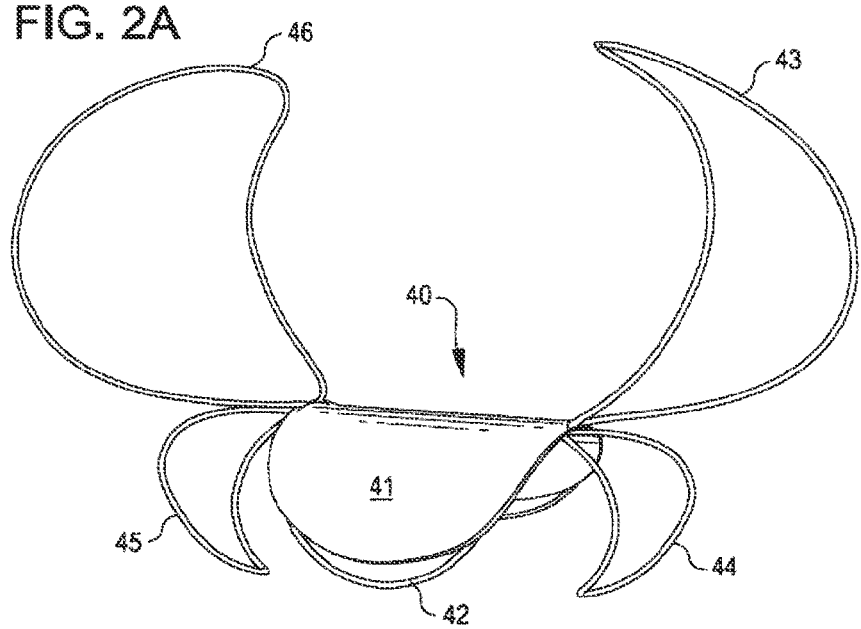
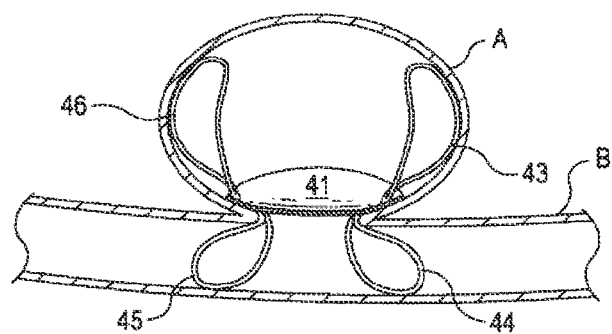
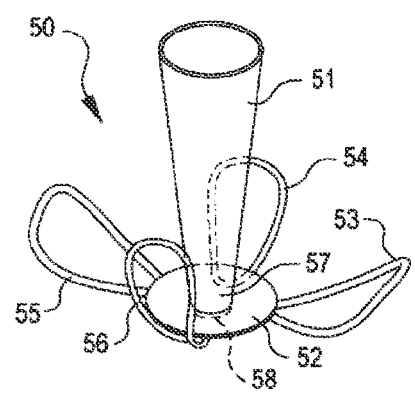
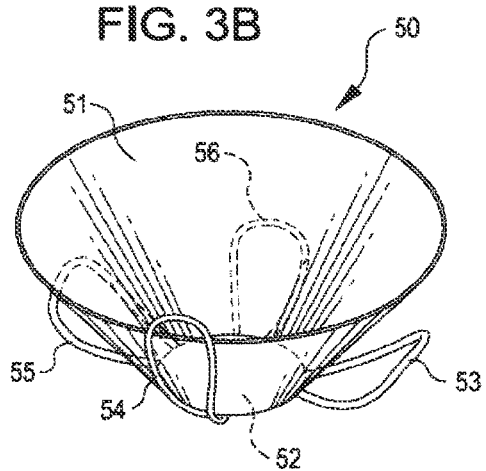

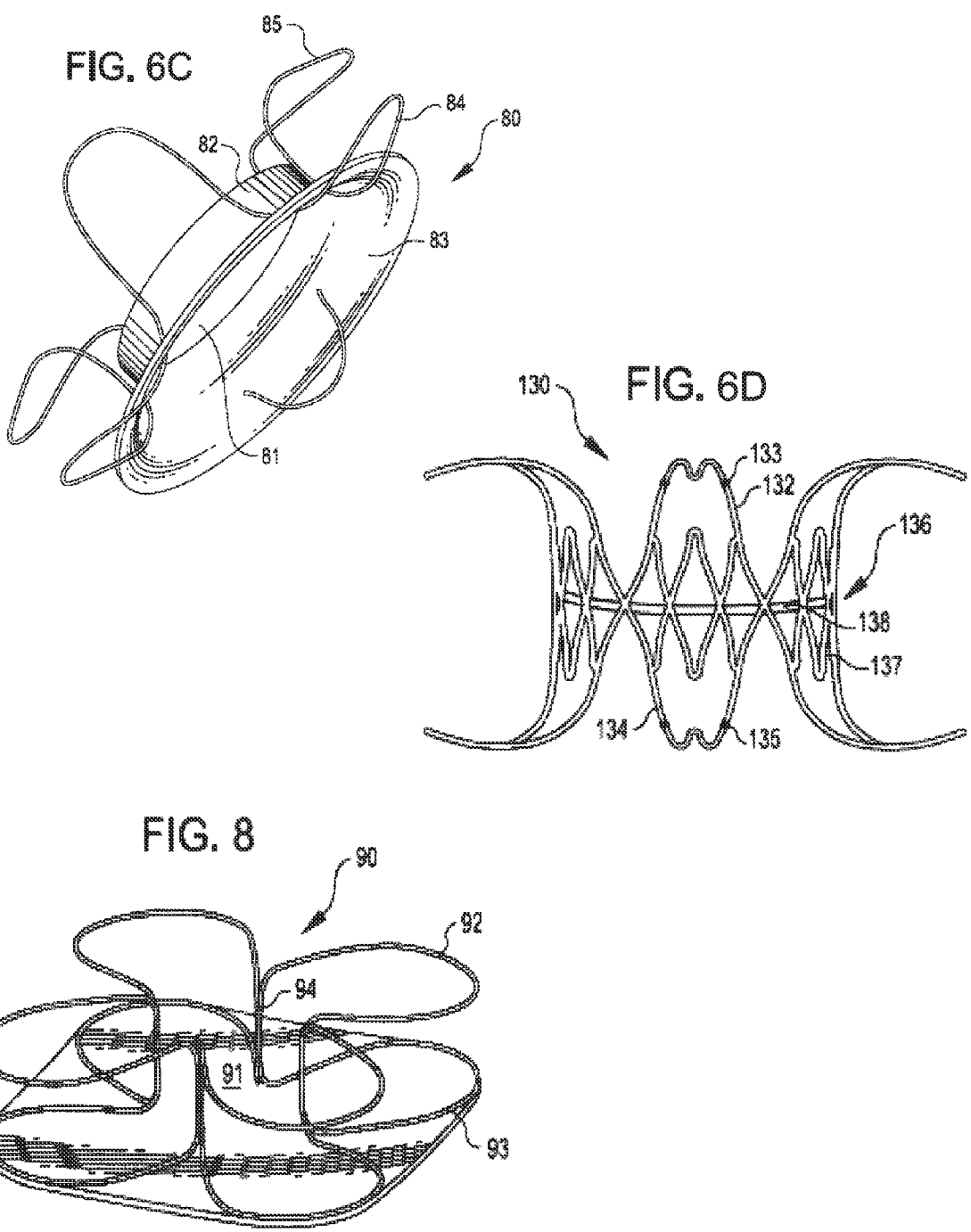

METHODS AND SYSTEMS FOR ENDOVASCULARLY CLIPPING AND REPAIRING LUMEN AND TISSUE DEFECTS

CROSS-REFERENCE TO RELATED APPLICATION(S)

This application claims priority to and is a continuation of U.S. patent application Ser. No. 11/737,700, filed Apr. 19, 2007, now U.S. Pat. No. 8,551,132, which claims priority to and is a continuation-in-part application of U.S. patent application Ser. No. 11/324,827, filed Jan. 3, 2006, now U.S. Pat. No. 8,545,530, which claims the benefit of U.S. Provisional Application No. 60/728,052, filed Oct. 19, 2005.

In addition, U.S. patent application Ser. No. 11/737,700, filed Apr. 19, 2007, claims priority to and is a continuation in part of International Patent App. No. PCT/US2006/40907, filed Oct. 18, 2006, which claims priority to U.S. Provisional Application Nos. 60/823,730, filed Aug. 28, 2006; 60/803,200, filed May 25, 2006; 60/747,400, filed May 16, 2006; and 60/728,052, filed Oct. 19, 2005.

The disclosures of all of these applications are incorporated herein by reference in their entireties.

TECHNICAL FIELD

The present invention relates generally to systems and methods for repairing defects in physiological lumens, such as defects in blood vessels or gas passageways of a mammal, using minimally invasive techniques. More specifically, the invention relates to systems and methods for occluding undesired openings, clipping and repairing defects in the anatomy of a human or animal, such as aneurysms, other blood vessel irregularities, septal defects and other tissue defects, and other passageway irregularities, using minimally invasive techniques.

BACKGROUND

Surgical techniques for closing openings and repairing defects in anatomical lumens and tissues, such as blood vessels, septal defects and other types of physiological irregularities and defects, are highly invasive. Surgical methods for clipping aneurysms, for example, require opening the skull, cutting or removing overlying brain tissue, clipping and repairing the aneurysm from outside the blood vessel, and then reassembling tissue and closing the skull. Surgical techniques for repairing septal defects are also highly invasive. The risks associated with anesthesia, bleeding and infection during and following these types of procedure are high, and tissue that is affected during the procedure may or may not survive and continue functioning.

Minimally invasive surgical techniques may alternatively be used to place occlusive devices within or across an opening or cavity in the body, such as in the vasculature, spinal column, fallopian tubes, bile ducts, bronchial and other air passageways, and the like. In general, an implantable device is guided to a desired site through a delivery catheter and may be pushed through an opening at the distal end of the delivery catheter by a pusher mechanism, such as a pusher or delivery wire, thereby deploying the device at the desired site of intervention. Once the occlusive device has been placed at the desired location, it is detached from the pusher mechanism without disturbing placement of the occlusive device or damaging surrounding structures.

Aneurysms are bulges in an artery wall, generally caused by a weakening in the artery wall, that form an opening or cavity and are often the site of internal bleeding and stroke. In general, the minimally invasive therapeutic objective is to prevent material that collects or forms in the cavity from entering the bloodstream, and to prevent blood from entering and collecting in the aneurysm. This is often accomplished by introducing various materials and devices into the aneurysm.

Various types of embolic agents and devices are used to reduce risks to a patient associated with the presence of an aneurysm. One class of embolic agents includes injectable fluids or suspensions, such as microfibrillar collagen, various polymeric beads and polyvinylalcohol foam. These polymeric agents may be cross-linked (sometimes in vivo) to extend the persistence of the agent at the vascular site. These agents are often introduced into the vasculature through a catheter. After introduction and at the site, the introduced materials form a solid space-filling mass. Although some of these agents provide for excellent short term occlusion, many are thought to allow vessel recanalization due to absorption into the blood. Other materials, such as hog hair and suspensions of metal particles, have also been proposed and used to promote occlusion of aneurysms. Polymer resins, such as cyanoacrylates, are also employed as injectable vaso-occlusive materials. These resins are typically mixed with a radiopaque contrast material or are made radiopaque by the addition of a tantalum powder. Accurate and timely placement of these mixtures is crucial and very difficult. These materials are difficult or impossible to retrieve once they have been placed in the vasculature.

Implantable vaso-occlusive metallic structures are also well known and commonly used. Many vaso-occlusive devices are provided in the configuration of helical coils and are constructed from a shape memory material that forms a desired coil configuration upon exiting the distal end of a delivery catheter. The purpose of the coil is to fill the space formed by a defect or injury and facilitate formation of an embolus with the associated allied tissue. Multiple coils of the same or different structures may be implanted serially in a single aneurysm or other vessel defect during a procedure. Implantable framework structures are also used in an attempt to stabilize the wall of the aneurysm or defect prior to insertion of filling material such as coils.

Techniques for delivering a vaso-occlusive device to a target site generally involve a delivery catheter and a detachment mechanism that detaches the coil from a delivery mechanism after placement at the target site. A microcatheter is initially steered through the delivery catheter into or adjacent to the entrance of an aneurysm, typically aided by the use of a steerable guidewire. The guidewire is then withdrawn from the microcatheter lumen and replaced by the implantable vaso-occlusive coil. The vaso-occlusive coil is advanced through and out of the microcatheter and thus deposited within the aneurysm or other vessel abnormality. Implantation of the vaso-occlusive device within the internal volume of a cavity and maintenance of the device within the internal volume of the aneurysm is crucial. Migration or projection of a vaso-occlusive device from the cavity may interfere with blood flow or nearby physiological structures and poses a serious health risk.

One type of aneurysm, commonly known as a "wide neck aneurysm" is known to present particular difficulty in the placement and retention of vaso-occlusive coils. Wide neck aneurysms are generally referred to as aneurysms of vessel walls having a neck or an entrance zone from the adjacent vessel that is large compared to the diameter of the aneurysm or that is clinically observed to be too wide to effectively retain vaso-occlusive coils deployed using the techniques discussed above.

The placement of coils, or other structures or materials, in the internal space of an aneurysm or other defect has not been entirely successful. The placement procedure may be arduous and lengthy, requiring the placement of multiple devices, such as coils, serially in the internal space of the aneurysm. Longer procedures, in general, involve higher risks of complication from anesthesia, bleeding, infection, and the like. Moreover, because placement of structures in the internal space of an aneurysm doesn't generally completely occlude the opening, recanalization of the original aneurysm is more likely to occur, debris and occlusive material may escape from within the aneurysm and present a risk of stroke, vessel blockage or other undesirable complications. Blood may also flow into aneurysm and other blood vessel irregularities after the placement of embolic devices, which increases the risks of complication and further enlargement of the aneurysm. Furthermore, some aneurysms, vessels and other passageway defects are not well-suited to placement of coils or other conventional occlusive devices.

Devices for maintaining vaso-occlusive coils within an aneurysm have been proposed. One such device is described in U.S. Pat. No. 5,980,514, which discloses devices that are placed within the lumen of a feed vessel exterior to the aneurysm to retain coils within the aneurysm cavity. The device is held in place by means of radial pressure of the vessel wall. After the device is released and set in an appropriate place, a microcatheter is inserted into the lumen behind the retainer device and the distal end of the catheter is inserted into the aneurysm cavity for placement of one or more vaso-occlusive devices. The retainer device prevents migration of occlusive devices from the cavity.

Another methodology for closing an aneurysm is described in U.S. Pat. No. 5,749,894, in which a vaso-occlusive device, such as a coil or braid, has on its outer surface a polymeric composition that reforms or solidifies in situ to provide a barrier. The polymer may be activated, e.g. by the application of light, to melt or otherwise to reform the polymer exterior to the vaso-occlusive device. The vaso-occlusive device then sticks to itself at its various sites of contact and forms a rigid whole mass within the aneurysm.

Devices for bridging the neck of an aneurysm have also been proposed. U.S. Patent Application 2003/0171739 A1, for example, discloses a neck bridge having one or more array elements attached to a junction region and a cover attached to the junction region and/or the array elements. The array elements may comprise Nitonol alloy loops and the cover may comprise a fabric, mesh or other sheeting structure.

U.S. Patent Application 2004/087998 A1 discloses a device and method for treatment of a vascular defect in which two sheets, or a sheet and a strut structure function to secure the vaso-occlusive device and to occlude an opening. This patent publication lists numerous biocompatible compositions and materials that may be used in connection with the device to promote adhesion, fibrosis, tissue growth, endothelialization or cell growth.

U.S. Patent Application 2004/0193206 A1 discloses another device for at least partially occluding an aneurysm including a plurality of elongate members configured to move relative to one another to transform the bridge between the delivery and deployed configurations. A two array bridge, in which a first array is deployed inside the aneurysm and a second array is deployed outside the aneurysm is also disclosed.

Septal defect closure devices are also well known. Such devices occlude openings, or septal defects, in the heart or the vascular system. Septal closure devices are disclosed, for example, in U.S. Pat. Nos. 6,077,291 and 6,911,037. Bronchial flow control devices that seal or partially seal a bronchial lumen are also known, see, e.g., U.S. Pat. No. 7,011,094.

Systems currently used for the detachment of implantable devices after placement include mechanical systems, electrolytic systems and hydraulic systems. In mechanical systems, the occlusive device and the pusher wire are linked by means of a mechanical joint, or inter-locking linkage, which separates once the device exits the delivery catheter, thereby releasing the device. Examples of such systems include those taught in U.S. Pat. Nos. 5,263,964, 5,304,195, 5,350, 397, and 5,261,916.

In electrolytic systems, a constructed joint (generally either fiber- or glue-based) connects the pusher wire to the occlusive device. Once the device has been placed in the desired position, the joint is electrolytically disintegrated by the application of a current or heat (for example, using a laser) by the physician. An example of such a system is provided in U.S. Pat. No. 5,624,449. Such systems have the disadvantage that dissolved material or gases generated by electrolysis may be released into the vasculature, thus presenting a potential hazard to the patient. Electrolytic detachment may also take more time to accomplish than is desirable during an interventional operation in which several occlusive devices are placed.

In hydraulic systems, the pushing wire is connected to the occlusive device by means of a polymer coupling. The pushing wire contains a micro-lumen to which the physician attaches a hydraulic syringe at the proximal end of the pusher wire. Upon the application of pressure on the syringe plunger, the hydraulic pressure increases and forces the polymer joint to swell and break, thereby releasing the device. An example of a hydraulic system is that described in U.S. Pat. No. 6,689,141.

Despite the numerous devices and systems available for occluding physiological defects using minimally invasive techniques, these procedures remain risky and the results, even if successful in terms of occluding an opening, rarely restore the physiological structure to its normal, healthy condition. Methods and systems of the present invention are directed, among other things, to reducing the length and complexity of minimally invasive procedures for occluding openings and repairing a lumen or tissue defect, and to restoring a physiological structure, such as a blood vessel, to its normal, healthy condition.

SUMMARY

The present invention provides methods and systems for repairing an opening in an internal lumen or cavity within a subject's body using minimally invasive techniques. In general, these systems and methods are used in connection with vascular abnormalities such as openings or cavities and are described herein with reference to their application to aneurysms and other types of blood vessel defects. It will be appreciated, however, that systems and methods of the present invention are not limited to these applications and may be employed in a variety of medical indications in which repair and reconstruction of an opening or cavity in a physiological lumen or passageway or tissue is desired.

In one aspect, methods and systems of the present invention provide repair and reconstruction of a lumen, such as a blood vessel, by placement of a closure structure across an opening or cavity and retention of the closure structure across the opening using one or more anchoring structures that serve as a means of endovascularly clipping the opening or cavity, such as an aneurysm, and excluding it from the parent artery. Following placement, the closure structure substantially covers the opening or cavity and forms a generally continuous lumen wall that is substantially similar to the conformation of the lumen wall in its healthy condition. Neither the anchoring nor the closure structures interferes substantially with the fluid flow in the lumen. Various agents, such as agents that promote re-endothelialization and tissue growth, as well as bonding agents, therapeutic agents, anti-thrombolytic agents and the like may be provided to the repair site during or following the placement procedure and/or in association with the system.

In another aspect, methods and systems of the present invention provide exclusion of a defect, such as an aneurysm, by placement of a closure structure that restricts access to and cellular communication with the defect across an opening or cavity and retention of the closure structure across the opening using one or more anchoring structures. Methods and systems of the present invention may further promote shrinking and reabsorption of the defect, or portions of the defect, and facilitate hemostasis inside the defect. In one aspect, methods and systems of the present invention for treatment of aneurysms not only restore the structure and function of the parent vessel in the vicinity of the defect, but also stabilize material inside the aneurysm, prevent debris from escaping into the bloodstream, and promote a reduction in the size and mass of the aneurysm.

Endoluminal and endovascular procedures are commonly used for placing implantable devices and materials in many types of interventions. An intravascular guide catheter is generally inserted into a patient's vasculature, such as through the femoral artery, and guided through the vasculature to, or approaching, a desired site of intervention. Additional delivery mechanisms and specialized catheters, such as microcatheters, pusher devices and the like, may be used to facilitate delivery of various devices and accessories to the target site. Implantable devices are generally detachably mounted to a pusher or delivery mechanism and navigated through the guide catheter to the target site, where they are deployed and detached from the delivery mechanism. The delivery mechanism is then withdrawn through the guide catheter and additional devices, accessories, drugs or the like may be delivered to the target site, if desired, prior to removal of the guide catheter.

Methods of the present invention involve navigation of a device incorporating a closure structure and one or more anchoring structures in a small diameter, delivery condition to a desired repair site using minimally invasive, endoluminal techniques. In some embodiments, a guidewire is introduced and navigated through the guide catheter to the target repair site. The closure device may then be navigated to the target repair site and deployed over the guidewire. In a preferred embodiment, the closure device is preloaded in the distal portion of a delivery catheter sized for navigating physiological lumen(s) to the target repair site. The combination of the guidewire, the delivery catheter, the closure device and a pusher or detachment device is sized appropriately and has adequate flexibility and pushability to navigate relatively long lumen distances and tortuous pathways, if necessary. Long and tortuous pathways must be traversed, for example, to deliver implantable devices to the cerebrovasculature, and both the delivery catheter(s) and the implantable devices must be sized and configured to provide the required flexibility, pushability and guidance.

In one embodiment, methods of the present invention further involve guiding and positioning a defect closure system having a closure structure and at least two sets of anchoring structures in proximity to a physiological defect or opening in a small diameter delivery condition. In general, a first anchoring structure, or a first set of anchoring structures, is positioned and deployed in contact with or in proximity to one surface near the physiological defect or opening. Upon deployment, the first anchoring structure(s) unfold and extend radially to assume the conformation of a generally circumferential structure larger than the defect or opening and positioned generally around the periphery of the closure structure. The closure structure is then positioned and deployed across the physiological defect or opening to substantially cover and occlude the defect or opening. Following deployment of the closure structure, a second anchoring structure, or a second set of anchoring structures, is positioned and deployed in contact with or in proximity to another, generally opposed surface of the physiological defect or opening. The second anchoring structure or set of anchoring structures unfolds and extends radially to assume the conformation of a generally circumferential structure, larger than the defect or opening and positioned generally around the periphery of the closure structure on the opposite surface of the tissue (e.g., vessel wall) from the first anchoring structure(s). The anchoring structures in a deployed condition are preferably positioned in contact with or closely adjacent opposite surfaces of the lumen or tissue near the defect or opening, and the closure structure preferably substantially covers an opening and conforms to the structure and configuration of the lumen wall or the defect being closed to restore it to its normal, healthy structure and configuration. The anchoring structures effectively serve as opposing clips, contacting opposed surfaces of the defective structure, or extending to contact healthy tissue in proximity to the defect, to position and retain the closure structure in place across an opening.

Deployment of the defect closure system may be aided by placement of radiopaque markers on the delivery catheter and/or the defect closure system. One or more radiopaque markers may be provided, for example, at a distal end of the device (when in a delivery condition), which corresponds to a first anchoring structure; at an intermediate portion of the device (when in a delivery condition), corresponding to the closure structure; and/or at a proximal portion of the device (when in a delivery condition), corresponding to a second anchoring structure. The device may then be deployed by positioning the distal radiopaque marker across the defect opening and in the internal space of an opening or cavity in proximity to the opening and deploying a first anchoring structure; positioning an intermediate radiopaque marker at the defect opening and deploying the closure structure; and finally positioning the proximal radiopaque marker slightly outside the opening and deploying the second anchoring structure. The use and placement of radiopaque markers in connection with the closure device and/or delivery catheter facilitates accurate positioning and deployment of the anchoring and closure structures. The closure system is securely positioned and retained by positioning the anchoring structures on opposite faces of the lumen or tissue near the opening in a circumferential manner and positioning the closure structure across the opening. The position of the closure system may be monitored following placement and post-treatment by examining the position of the radiopaque markers provided on the device with respect to the tissue defect or opening.

Implantable devices of the present invention employ a closure structure to substantially cover, occlude and extend over an opening or cavity in tissue. The closure structure may be constructed from a variety of disparate materials, as described below, and may be provided with a variety of surface treatments and/or associated with a variety of materials to provide properties desired for various applications. The size and configuration of the closure structure in the deployed condition is preferably larger in at least one dimension than the opening of the defect, such as an aneurysm neck, so that the closure structure substantially covers the opening when deployed. The closure structure may have a substantially continuously occlusive surface area or, in alternative embodiments, may have one or more openings to facilitate placement using a co-axial guidewire and/or to facilitate delivery of supplemental implantable devices or agents to the interior of the cavity or defect following placement of the closure structure.

The closure structure, in some embodiments, is semipermeable and has generally radial flexibility sufficient to mimic the structure and movement (e.g. pulsatility) of the vessel wall or other physiological structure it's repairing. When the closure structure is placed across the neck of an aneurysm, for example, it becomes substantially continuous with and follows the motion of the vessel wall, providing effective repair and reconstruction of the vessel wall and restoring strength, structure and flexibility to the vessel wall. In a preferred embodiment, the closure structure and/or anchoring structures, after placement across a tissue or vessel defect, not only effectively repair the defect, but promote cellular ingrowth and reendothelialization, thereby further incorporating the closure device in the physiological structure and reducing the opportunity for the structure to weaken and return to a structurally or functionally defective condition.

The closure structure may incorporate a reinforcing structure throughout its surface area, or in particular areas of its structure. In one embodiment, for example, a resilient and flexible sheet material may be bonded to or associated with a more rigid reinforcing structure having a regular or irregular pattern. In one embodiment, a closure structure is supported in the area of its perimeter by a wire loop or framework structure that provides structure and reinforcement and may, additionally or alternatively, incorporate one or more anchoring structures. The reinforcement structure, in one embodiment, comprises a collar structure that is integral with one or more anchoring structures, or serves as a mounting structure for one or more anchoring structures.

In some embodiments, the anchoring structure(s) biases a closure structure against the lumen wall and across an opening or defect from a position inside or outside the lumen wall. In some embodiments, multiple anchoring structures are provided that bias a closure structure against the lumen wall and across an opening or defect from positions both inside and outside the lumen wall. In yet other embodiments, multiple anchoring structures are provided, with at least one anchoring structure contacting or in close proximity to an internal lumen wall in proximity to the opening or defect and at least one anchoring structure contacting or in close proximity to an external lumen wall or an internal wall of a cavity or defect in the lumen. In one embodiment, anchoring structures are positioned circumferentially both inside and outside a lumen defect in proximity to an opening or defect, and a closure structure is positioned across the opening or defect, substantially covering the opening or defect, effectively excluding one side of the opening from the other and restoring the lumen to its original closed and continuous structure.

In some embodiments, the anchoring structures are intended to at least partially contact one or both sides of a tissue or vessel wall in proximity to an opening or defect to position and support the closure structure across the opening. The anchoring structures are generally atraumatic and maintain the closure structure in position occluding the defect without damaging the neighboring tissue or restricting blood flow in the vessel or tissue. In one embodiment, anchoring structures are provided as loop or clip structures with openings and generally have a material density over their surface area that is less than the density of the closure structure over its surface area. The implantable device is generally in a small diameter, generally cylindrical configuration in a delivery condition and, in this condition, the anchoring structures generally project in opposite directions from the intermediate closure structure. During deployment, the anchoring structures change shape and open outwardly, in a circumferential fashion, to form a larger diameter circumferential anchoring structure. Distal and proximal anchoring structures (as positioned in a delivery condition), which are deployed on opposite sides of a cavity or defect, may have substantially the same configuration and dimensions, or the anchoring structures may be designed to have varying lengths, varying configurations, varying structures, and the like. In some embodiments, the anchoring structures positioned inside and outside the lumen defect are substantially aligned with one another, while in some embodiments, the anchoring structures positioned inside and outside the lumen defect are substantially staggered or offset with respect to one another.

In another embodiment, the implantable device comprises a closure structure, substantially as described above, in combination with one or more anchoring structure(s) and/or collar or retaining structures. In this embodiment, an anchoring structure comprises at least two positioning loops mounted on, or otherwise associated with, the closure structure. The positioning loops, in a deployed condition, are configured and sized to contact interior walls of the aneurysm and/or blood vessel walls in proximity to the aneurysm, and to bias the closure structure against the wall of the aneurysm or against blood vessel walls in proximity to the neck of the aneurysm, thereby retaining the closure structure in place substantially covering the neck of the aneurysm.

In a deployed condition, the closure structure and the anchoring structure(s) may be positioned inside and/or outside the neck of the aneurysm. In one embodiment, for example, the implantable device is deployed in the interior of an aneurysm such that opposed anchoring structures contact the interior wall of the aneurysm and the closure structure substantially covers the entrance or neck of the aneurysm, with the perimeter of the closure structure being in the interior of the aneurysm or contacting the vessel wall in proximity to the neck of the aneurysm. In another embodiment, the implantable device is deployed in the blood vessel at the aneurysm such that anchoring structure(s) contacts the wall of the blood vessel, with the perimeter of the closure structure substantially covering the neck of the aneurysm and contacting the blood vessel wall in proximity to the neck of the aneurysm. Depending on the configuration of the anchoring structure(s), multiple anchoring loops may be positioned contacting or in close proximity to the vessel wall near and/or generally opposite the neck of the aneurysm following deployment.

In yet another embodiment, the implantable device comprises a closure structure having a substantially tapered or truncated conical portion joined to a closure membrane and an anchoring structure comprising at least two positioning members. In this embodiment, the tapered portion of the closure structure preferably comprises a discontinuous mesh structure constructed from a shape change metallic material that, during deployment, expands to contact at least a portion of the internal wall of the aneurysm. The base of the tapered, discontinuous mesh structure is preferably joined to or associated with a closure membrane that, in a deployed condition, substantially covers the neck of the aneurysm. Anchoring structures are associated with the closure structure and may comprise a plurality of positioning loops that, in a deployed condition, contact at least a portion of a vessel wall in proximity to the neck of the aneurysm. According to another embodiment, the anchoring structures have at least two petal-like structures comprising, for example, metallic structures associated with permeable or impermeable coverings. According to yet another embodiment, the anchoring structure may comprise a second tapered, discontinuous mesh structure having a shallower configuration than that of the closure structure.

The closure structure placed across the neck of the aneurysm may have a central opening or slot for passage of a guidewire of another delivery or targeting mechanism, or for introduction of compositions, devices, or the like subsequent to placement of the closure system. According to some methods of the present invention, additional embolic devices such as coils, liquid or particulate embolics, or the like, may be introduced through a delivery catheter inserted through an opening of the closure structure following placement of the closure structure. In some embodiments, the additional embolic substances and/or devices may act to bias the perimeter of the closure device against the interior wall of the aneurysm and thereby assist in retaining the closure structure in position substantially covering the neck of the aneurysm.

Implantable devices disclosed herein may be delivered to the target site through a delivery catheter using a pusher delivery system and/or detachment mechanism. The closure structure, supporting framework and anchoring structures are generally radially compressed along the delivery axis and arranged in a substantially cylindrical configuration in a delivery condition. In embodiments that utilize a pusher system, the pusher is located proximal to the proximal anchoring devices and can translate the closure device in relationship to the delivery catheter. Deployment may be achieved by a combination of actively pushing the device out of a delivery catheter and actively withdrawing the delivery catheter while maintaining the device in a stationary condition. In an alternative embodiment, implantable devices incorporate a detachment element that is released or detached following deployment. Detachment mechanisms known in the art, including mechanical, electrolytic, hydraulic and other systems, may be utilized for deployment of the implantable devices disclosed herein.

In one deployment system, a device wire is mounted on or associated with an implantable device of the present invention. A proximal end of the device wire is mountable on, or in proximity to, a detachment mechanism comprising a shape change activation element having a generally linear configuration and being fixedly connected at its proximal end to a delivery wire, conduit, catheter or the like. The proximal end of the device wire and the distal end of the activation element have mating attachment mechanisms that, in a delivery condition, provide reliable attachment and guidance of the implantable device to the desired detachment site. Detachment of the activation element from the device wire following placement of the device at a desired location is accomplished by applying a shape change force, such as heat or current, to the activation element, producing a shape change in the activation element that releases the device wire, allowing withdrawal of the activation element and delivery wire.

BRIEF DESCRIPTION OF THE DRAWINGS

Various aspects of applicants' claimed inventions are illustrated schematically in the accompanying drawings, which are intended for illustrative purposes only and are not drawn to scale.

FIG. 2A illustrates an enlarged schematic front perspective view of another implantable closure device in a deployed condition and FIG. 2B schematically illustrates the deployment of the implantable closure device of FIG. 2A at a vessel irregularity.

FIGS. 3A and 3B illustrate enlarged schematic front perspective views of another implantable closure device, with the device of FIG. 3A in a partially deployed condition and the device of FIG. 3B in a fully deployed condition.

FIG. 4A shows the implantable closure device being inserted into the neck of an aneurysm; FIG. 4B shows the device of FIG. 3B (in dashed lines) in a deployed condition inside an aneurysm and blood vessel; and FIG. 4C shows the device of FIG. 3B in a deployed condition inside an aneurysm with the aneurysm and blood vessel shown in cross-section.

FIGS. 6A-6D illustrate enlarged, schematic perspective views of implantable devices having a neck element with stabilizing structures in a substantially deployed condition.

FIG. 8 illustrates an enlarged, schematic side perspective view of an implantable device having opposed anchoring struts in a substantially deployed condition.

DETAILED DESCRIPTION

Figure 1A:
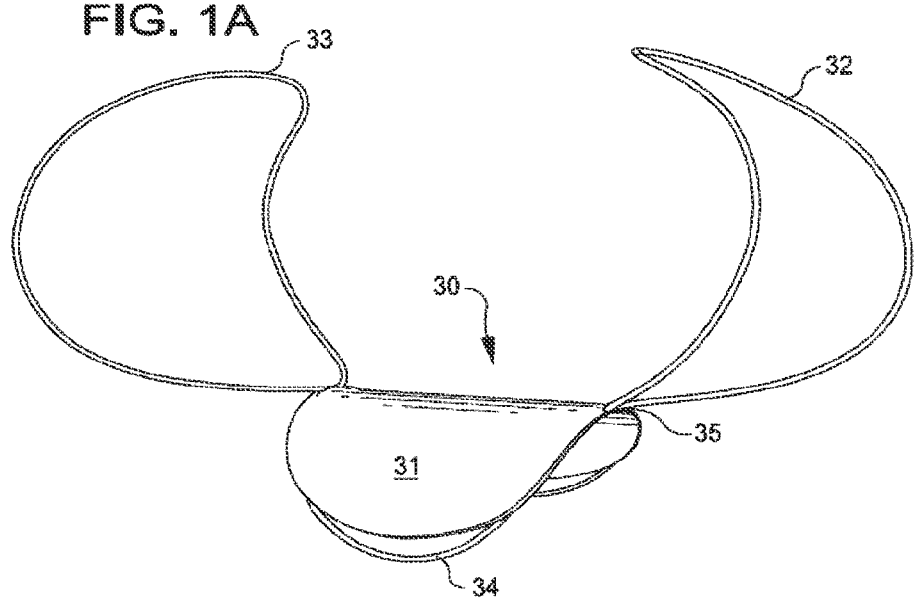
FIG. 1A illustrates an enlarged schematic front perspective view of one embodiment of an implantable closure device in a deployed condition.

Implantable systems of the present invention are described and illustrated, in detail, with respect to their application as aneurysm closure devices. It will be appreciated, however, that these systems are not limited to this application and may be adapted and utilized in connection with the treatment and repair of other vessel, tissue or air passageway cavities, abnormalities, or the like. Similarly, it will be appreciated that applicants' methods for repairing defects and openings are not limited to the systems described herein.

Implantable closure devices of the present invention generally comprise a closure structure that is placed across a tissue or vessel defect and an anchoring structure that positions and holds the closure structure in place. Many alternative embodiments and structures are disclosed herein. The flexible patch(es) or membrane(s) employed in the closure structures disclosed herein are generally constructed from a flexible material that can be delivered through a catheter in a small diameter delivery condition and, in a deployed condition, assumes a larger dimension configuration. In one embodiment, the closure structure is constructed from a material that is substantially impermeable to liquids such as blood and bodily fluids. Alternatively, the closure structure may be constructed from a material that is semi-permeable or permeable to liquids, such as blood and bodily fluids, and allows at least limited fluid exchange across the patch or membrane. The closure structure is impermeable to particulates having a larger diameter than the pore size of a fluid permeable membrane comprising the closure structure. The closure structure may have numerous configurations, depending on the device application, and may be generally circular, elliptical, oval, triangular, polygonal or the like.

The closure structure is constructed from material(s) that is biocompatible and biostable and that is compressible, foldable or otherwise deformable for assuming a low diametric profile in a delivery condition for loading into or mounting to a delivery catheter. Materials forming the closure structure may comprise, for example, many types of natural or synthetic polymeric materials, silicone materials, rubber materials, a woven or non-woven fabric material such as Dacron™, a fluoropolymer composition such as a polytetrafluoroethylene (PTFE) material such as TEFLON,® or an expanded polytetrafluoroethylene (ePTFE) material such as GORE-TEX®, SOFTFORM®, IMPRA® or the like, a polymeric material such as polyurethane, polyurethane/silicone combinations and copolymers, and the like. In another embodiment, a closure structure may comprise a metallic material, such as a thin-film shape memory alloy, e.g., a thin-film Nickel-Titanium alloy such as a Nitinol alloy. Multiple membrane layers and membranes comprising multiple components and compositions may be provided. In some embodiments, the closure structure is constructed from a material that is flexible and resilient and expands and contracts generally radially with the movement, or pulsatility, of the tissue or blood vessel in which it's placed.

In some embodiments, the closure structure comprises a mesh-like structure having a uniform or non-uniform configuration over its surface area. In general, closure structures having a mesh configuration have a generally fine mesh structure. In some embodiments, the closure structure has a mesh-like structure that is radially expandable. In other embodiments, the closure structure has a mesh-like structure that is expandable along one or more axes.

The closure structure may have a porous or perforated surface structure over at least a portion of its surface area, with pores arranged to provide a substantially uniform porosity over the surface area, or with pores arranged to provide different porosities at different surface areas of the closure structure. The average pore size may be substantially uniform over the surface area of the closure structure, or pores having different size distributions may be provided. In general, pore sizes in the range of from about 0.5 microns to 200 microns are suitable. In one embodiment, a pore structure is provided that permits flow of liquids across the closure structure but excludes large proteins and cells, including red blood cells. In general, pores having an average diameter of less than about 10 microns will exclude large proteins and cells, while allowing fluids to penetrate and cross the membrane. The arrangement of pores may form a regular or irregular pattern and the conformation of the pores may be uniform or non-uniform and may be generally circular, elliptical, square, or the like. A higher porosity may be provided, for example, at peripheral portions of the closure structure that, following placement, are in proximity to or contacting the tissue or vessel wall.

The closure structure may, alternatively or additionally, have a surface treatment provided on one or both sides that promotes cellular attachment and growth. In one embodiment, for example, the material forming the closure structure has a surface conformation that is irregular, or roughened, or incorporates surface irregularities that promote cellular attachment to the material. In another embodiment, the closure structure may have a three dimensional configuration that incorporates depressions, grooves, channels, or the like, in a regular or irregular pattern, to promote cellular attachment and re-endothelialization.

In some devices disclosed herein, the closure structure and/or other components of the implantable device, including one or more anchoring structures, are structured or treated to promote, or comprise a material or substance(s) that promotes, cellular ingrowth or attachment at the site of deployment. Similarly, methods of the present invention may involve introduction of agent(s) that promote cellular ingrowth and re-endothelialization at the site of the device deployment prior to, during, and/or subsequently to placement of the implantable device. For vascular applications, for example, it is desirable for some applications to promote the re-endothelialization of the blood vessel at the site of an aneurysm or another vessel defect that may be repaired by placement of devices of the present invention. Numerous substances that may be used in connection with methods and systems of the present invention are described in U.S. Patent Publications 2004/087998 A1 2004/0193206 A1, which are incorporated herein by reference in their entireties.

Numerous materials may be administered prior to, during or subsequent to device deployment, or associated with the implantable device, to promote cellular ingrowth. Biocompatible materials may be used for this purpose including, for example, proteins such as collagen, fibrin, fibronectin, antibodies, cytokines, growth factors, enzymes, and the like; polysaccharides such as heparin, chondroitin; biologically originated crosslinked gelatins; hyaluronic acid; poly($\alpha$-hydroxy acids); RNA; DNA; other nucleic acids; polyesters and polyorthoesters such as polyglycolides, polylactides and polylactide-co-glycolides; polylactones including polycaprolactones; polydioxanones; polyamino acids such as polylysine; polycyanoacrylates; poly(phosphazines); poly(phosphoesters); polyesteramides; polyacetals; polyketals;

polycarbonates and polyorthocarbonates including trimethylene carbonates; degradable polyethylenes; polyalkylene oxalates; polyalkylene succinates; chitin; chitosan; oxidized cellulose; polyhydroxyalkanoates including polyhydroxybutyrates, polyhydroxyvalerates and copolymers thereof, polymers and copolymers of polyethylene oxide; acrylic terminate polyethylene oxide; polyamides; polyethylenes; polyacrylonitriles; polyphosphazenes; polyanhydrides formed from dicarboxylic acid monomers including unsaturated polyanhydrides, poly(amide anhydrides), poly(amide-ester) anhydrides, aliphatic-aromatic homopolyanhydrides, aromatic polyanhydrides, poly(ester anhydrides), fatty acid based polyanhydrides, and the like; as well as other biocompatible or naturally occurring polymeric materials, copolymers and terpolymers thereof, fragments of biologically active materials; and mixtures thereof.

Some biocompatible polymers are considered to be bioabsorbable and are suitable for use in association with devices and methods of the present invention, including polylactides, polyglycolides, polylactide-co-glycolides, polyanhydrides, poly-p-dioxanones, trimethylene carbonates, polycaprolactones, polyhydroxyalkanoates, and the like. Biocompatible polymers which are not generally considered to be biodegradable may also be used, including polyacrylates; ethylene-vinyl acetates; cellulose and cellulose derivatives including cellulose acetate butyrate and cellulose acetate propionate; acyl substituted cellulose acetates and derivatives thereof; non-erodible polyolefins; polystyrenes; polyvinyl chlorides; polyvinyl fluorides; polyvinyl (imidazoles); chlorosulphonated polyolefins; polyethylene oxides; polyethylene glycols; polyvinyl pyrrolidones; polyurethanes; polysiloxanes; copolymers and terpolymers thereof, and mixtures thereof. Exemplary polymers are well known in the art and one of ordinary skill in the art would understand that such polymers are by far too numerous to list here. Thus, this list is intended for illustrative purposes only and is not intended to be exhaustive.

Non-polymeric materials may also be used on connection with closure systems of the present invention. Suitable non-polymeric materials include, for example, hormones and antineoplastic agents. Examples of other biocompatible materials which promote integration with the vasculature of the patient include, for example, processed human or animal tissue including, for example, cells or cell fragments, engineered vascular tissue, matrix material from bladder, stomach, liver, genetic material of a natural or synthetic origin, and the like.

Other types of compositions may also be associated with a closure structure or anchoring structure(s) forming the closure systems of the present invention. Hydrophilic and/or hydrophobic agents or bonding agents may be provided on all or a portion of the structure(s), for example. Similarly, friction-reducing agents, including fluoropolymers such as PTFE, may be provided on all or a portion of the structure(s) to facilitate deployment from a delivery catheter or sheath. Radiopaque markers or radiopaque compounds may be associated with certain structures or portions of device structure to facilitate accurate positioning, placement and monitoring of the deployed device. In one embodiment, for example, a radiopaque composition may be incorporated in the closure structure or provided as a coating on the closure structure. In yet another embodiment, certain therapeutic agents, antibiotic agents, thrombogenic agents, anti-thrombogenic agents, and the like may be associated with certain structures or portions of the device structure, or may be administered prior to, during or following deployment of the implantable device. Suitable agents are well known in the art and are used in connection with other types of implantable devices.

The closure structure may comprise multiple layers, and may have a variety of coatings or other materials associated with it, such as adherent or bonding substances, therapeutic substances, hydrophilic or hydrophobic materials, swellable materials such as hydrogels, radiopaque markers, and the like. In one embodiment, for example, a swellable hydrogel may be provided on a surface of the closure structure and/or anchoring structures that, in a deployed condition, face or contact an internal portion of an aneurysm. In another embodiment, an agent or combination of agents that promote embolization or thrombosis may be provided on a surface of the closure structure and/or anchoring structures that, in a deployed condition, face or contact an internal portion of an aneurysm to promote embolization inside the aneurysm. In yet another embodiment, an agent or combination of agents that reduce thrombosis and clotting, such as heparin, tissue plasminogen activator (tPA), Abciximab, and the like may be provided on a surface of the closure structure and/or anchoring structures that, in a deployed condition, face or contact a blood vessel or blood vessel wall. In still another embodiment, an agent or combination of agents that prevent restenosis and/or reduce inflammation to the site, such as Paclitaxel or a derivative or analog, Sirolimus, anti-inflammatory compositions such as steroids, statins, ibuprofen or the like, may be provided on a surface of the closure structure and/or anchoring structures. In yet another embodiment, a radioactive composition may be associated with a surface of the closure structure and/or anchoring structures for therapeutic or imaging purposes.

The membrane forming the closure structure may have a substantially continuous surface area or may be provided with one or more openings or slots that facilitate placement of the implantable device or mounting of the device on a catheter or delivery system in a delivery condition. The membrane is secured to a framework or anchoring structure preferably comprising a shape change material, such as a shape memory alloy, by forming, bonding, suturing, embedding, or the like. Some membrane materials may also be applied over or to a framework or anchoring structure by coating, dip coating, and the like.

Framework components supporting the closure structure, such as anchoring structures and reinforcing structures, may be constructed from a biocompatible shape change material that exhibits super-elastic behavior and/or shape memory properties, such as shape memory alloys. The shape change material changes shape in a predictable manner upon application of a shape change force such as heat, current or the like, to assume its predetermined, deployed condition. The force for producing the shape change is generally a change in temperature produced, for example, by introducing the device into a body temperature environment, by applying heat to the device using an external heating mechanism, or by heating the device by applying current through a conductive element. Upon heating of the shape memory material to, or above, a phase transition temperature of the material, the device framework structure and/or anchoring structure(s) assume their predetermined, larger dimension configuration.

Nitonol alloy alloys exhibiting super-elastic behavior and shape memory properties are preferred shape memory alloys for use in devices of the present invention. Framework and anchoring structures may be formed, for example, from solid wire, tubular wire, braided materials, or the like, and/or may be cut from a tube or cylindrical structure. Framework and anchoring structures may incorporate additional materials and may have coatings or membranes provided between and among the framework structures. In one embodiment, the framework and anchoring structures may be formed from a thin-film shape memory alloy, such as a thin-film Nitinol alloy, using sputtering techniques that are known in the art and described below.

The implantable device is generally delivered to a target site using a delivery catheter or a specialized microcatheter (referred to as a "delivery catheter") with a pusher catheter or rod, or using a pusher system incorporating a detachment mechanism. In one system, for example, the closure structure is detachably mounted to the distal end of a delivery catheter in a low profile condition, and is covered and retained in the low profile condition by a retractable sheath. The delivery catheter may be positioned at or within the neck of an aneurysm using conventional techniques and, upon retraction of the sheath, the closure structure assumes its predetermined, deployed condition and is placed across the neck of the aneurysm. More specifically, in a first step upon retraction of a portion of the sheath, a first anchoring structure is deployed and positioned contacting or in proximity to tissue adjacent the aneurysm neck on the interior of the aneurysm; in a second step, a closure structure or membrane is positioned across and substantially covering the aneurysm neck; and upon complete retraction of the sheath, a second anchoring structure is deployed and positioned contacting or in proximity to the internal vessel wall adjacent the aneurysm neck.

FIG. 1A illustrates an embodiment of a closure device 30 comprising a patch or closure structure 31 mounted to or associated with two anchoring structures 32, 33. Suitable materials for construction of the closure structure or membrane are described above. Closure structure 31 is supported by a framework structure 34 provided at least in a perimeter portion of and attached to closure structure 31 by means of bonding, suturing, or the like. Framework structure 34 is mounted to or associated with wing-like anchoring structures 32, 33. Both framework structure 34 and anchoring structures 32, 33 preferably comprise a shape change material such as a Nitinol alloy material.

Anchoring structures 32, 33 may comprise a solid wire or tubular structure, or may be formed from a material having a braided construction or another mesh-like structure. The configuration of anchoring structures 32, 33 in a deployed condition is designed so that at least a portion of anchoring structures 32, 33 contact an inner wall of an aneurysm or an internal wall of an associated blood vessel following deployment. The configuration of anchoring structures 32, 33 may be generally circular, oblong, or otherwise form a curvilinear configuration, or they may form a polygonal configuration. In a preferred embodiment, as illustrated in FIG. 1A, anchoring structures 32, 33, are generally oblong curvilinear structures that curve outwardly from attachment joint 35 to framework structure 34 and then back inwardly toward one another at the end remote from attachment joint 35.

In the embodiment illustrated in FIG. 1A, anchoring loops 32, 33 are generally the same configuration and are generally the same dimension and are located generally opposite one another. In another embodiment, the anchoring structures may have different configurations and/or dimensions. In one embodiment, for example, one of the anchoring structures may be longer and/or wider than the other anchoring structure, or the anchoring structures may have different three-dimensional curvilinear or polygonal configurations. Although two anchoring structures 32, 33 are illustrated, it will be appreciated that additional anchoring structures may be provided. Anchoring structures are preferably arranged in a generally symmetrical fashion with respect to framework structure 34 and/or closure structure 31.

Figure 1B:
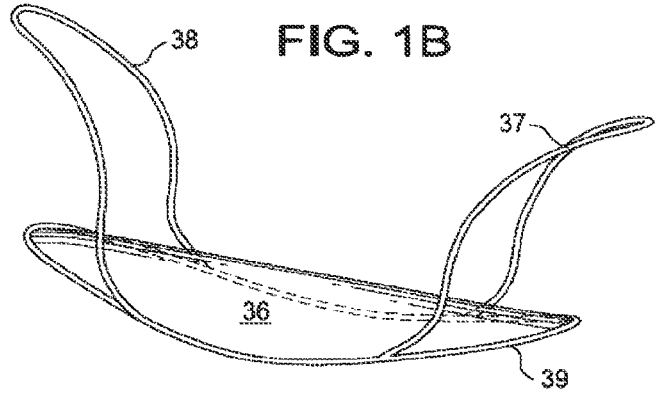
FIG. 1B illustrates an enlarged schematic front perspective view of another embodiment of an implantable closure device in a deployed condition.

FIG. 1B illustrates a similar closure device comprising a closure structure 36 having anchoring structures 37, 38 that attach to or project from a framework structure 39 along opposed, lateral edges of the framework structure. Closure structure 36 may optionally have an opening or slot provided in a generally central region. Anchoring structures 37, 38 as illustrated in FIG. 1B are gently curved and, at their terminal sections, extend beyond corresponding terminal sections of the framework structure and the closure structure. The closure and framework structures in this embodiment are generally provided having a surface area that exceeds the surface area of the aneurysm neck, and the anchoring structures generally reside inside the aneurysm following placement of the device. In this configuration, the anchoring structures exert lateral and downward force on the closure structure so that it generally conforms to the profile of the vessel wall at the site of the aneurysm, thereby sealing the neck of the aneurysm from flow in the vessel and providing reconstruction of the vessel wall at the site of the aneurysm.

Figure 1C:
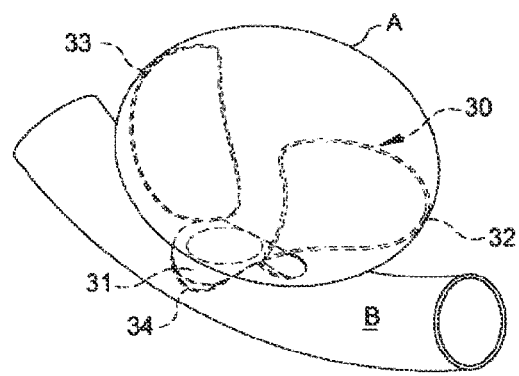
FIGS. 1C, 1D, 1E and 1F schematically illustrate the closure devices of FIGS. 1A and 1B deployed at the site of an aneurysm.
Figure 1D:
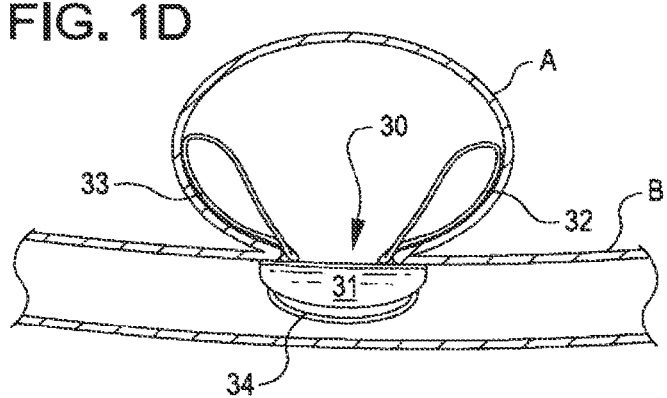
Figure 1E:
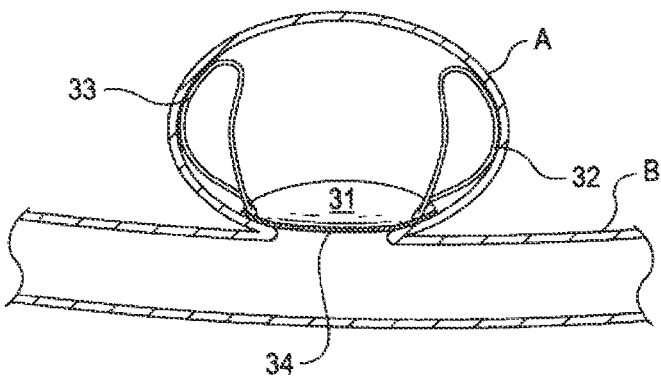

FIGS. 1C-1F schematically illustrate the closure devices of FIGS. 1A and 1B deployed at the site of an aneurysm. A bulge in blood vessel B forms an aneurysm A. As shown in FIGS. 1C and 1D, in one embodiment, when closure device 30 is deployed across the neck of and within aneurysm A, closure structure 31 is positioned to cover the opening of the aneurysm and anchoring structures 32 and 33 are retained inside and contact an inner aneurysm wall along at least a portion of their surface area. In this fashion, closure structure 31 and framework portion 34 are supported across the aneurysm opening and biased against the neck of the aneurysm from outside the aneurysm. In the embodiment illustrated in FIGS. 1C and 1D, closure structure 31 and framework portion 34 are deployed outside the internal space of the aneurysm. In an alternative embodiment illustrated in FIG. 1E, closure structure 31 and framework portion 34 are supported across the aneurysm opening and biased against the neck of the aneurysm from inside the aneurysm.

Figure 1F:
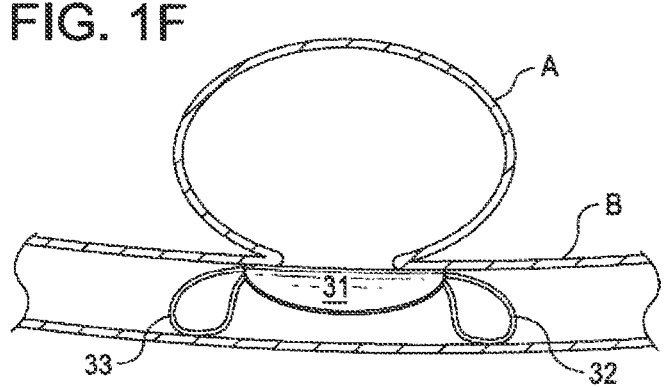

FIG. 1F illustrates an alternative deployment system and methodology, wherein a closure device having at least two anchoring structures is deployed such that closure structure 31 is positioned to cover the opening of the aneurysm and the anchoring structures 32, 33 are positioned outside the aneurysm and contact an inner blood vessel wall in proximity to the aneurysm. In this embodiment, anchoring structures 32, 33 may be generally sized and configured to match the inner diameter of the vessel in proximity to the neck of the aneurysm so that following deployment the anchoring structures contact the vessel wall in a substantially continuous manner without straining or enlarging the vessel wall in the area of the aneurysm. In all of these embodiments, following placement of the closure device, the closure structure substantially covers the aneurysm neck to effectively repair the vessel defect, and the anchoring structures do not substantially interfere with flow in the vessel.

FIG. 2A illustrates another closure device 40 comprising a closure structure 41 supported by a framework structure 42 and mounted to or associated with anchoring structures 43, 44, 45 and 46. The properties and configuration of closure structure 41 are generally as described above. Closure structure 41 is preferably supported by a framework structure 42 provided at least in a perimeter portion of structure 41 and attached to structure 41 by means of bonding, suturing, or the like. Framework structure 42 is mounted to or associated with two pairs of wing-like anchoring structures 43, 44 and 45, 46. Framework structure 42 and anchoring structures 43, 44, 45 and 46 preferably comprise a shape change material such as a Nitinol alloy material and may comprise a solid wire or tubular structure, or may be formed from a material having a braided construction or another mesh-like structure.

The configuration of anchoring structures 43, 44, 45 and 46, in a deployed condition, is designed so that at least a portion of each of anchoring structures 43, 44, 45 and 46 contacts an inner wall of an aneurysm or an inner wall of an associated blood vessel following deployment. The configuration of anchoring structures 43, 44, 45 and 46, in a deployed condition, may be generally circular, oblong, or otherwise form a curvilinear configuration, or they may form a polygonal configuration. In a preferred embodiment, as illustrated in FIG. 2A, anchoring structures 43, 44, 45 and 46 are generally oblong curvilinear structures that curve outwardly from an attachment joint to framework structure 42 and then back inwardly toward one another at the end remote from framework structure 42. In the embodiment illustrated in FIG. 2A, anchoring loops 43, 44, 45 and 46 form generally the same configuration and are generally the same dimension. Anchoring loops 43 and 46 are positioned in a generally mirror image orientation with respect to anchoring loops 44 45, respectively. Similarly, 43 and 44 are positioned in a generally mirror image orientation with respect to anchoring loops 46 and 45, respectively. In alternative embodiments, the configuration and/or dimension of each of anchoring loops 43, 44, 45 and 46 may vary and the configuration and/or dimension of each of anchoring loops 43, 44, 45 and 46 may be different. Although two pairs of generally opposed anchoring structures are illustrated, it will be appreciated that additional anchoring structures or pairs of opposed anchoring structures may be provided. Anchoring structures are preferably arranged in a generally symmetrical fashion with respect to framework structure 42 and/or closure structure 41.

FIG. 2B illustrates a closure device of the type shown in FIG. 2A deployed such that patch 41 is positioned to cover the opening of the aneurysm, with two of the anchoring structures positioned inside the aneurysm, contacting at least a portion of the aneurysm wall, and two of the anchoring structures positioned outside the aneurysm, contacting an inner blood vessel wall in proximity to the aneurysm. Methods for repairing a vessel using a closure device of the type shown in FIG. 2A generally involve deploying a first anchoring structure comprising, for example, anchoring loops 43, 46 inside the neck of aneurysm A, and positioning anchoring loops 43, 46 in proximity to or contacting the internal aneurysm wall near the aneurysm neck; deploying the closure structure 41 across the neck of the aneurysm to substantially cover the aneurysm neck; and deploying a second anchoring structure comprising, for example, anchoring loops 44, 45, outside the aneurysm neck and positioning anchoring loops 44, 45 in proximity to or contacting the internal blood vessel wall near the aneurysm neck.

Alternative embodiments of aneurysm closure devices are illustrated in a partially deployed condition in FIG. 3A and a fully deployed condition in FIG. 3B. In this embodiment, closure device 50 comprises a tapered closure structure 51 having a generally truncated conical configuration joined to a closure membrane 52 having the properties of the closure structure described above, and having an anchoring structure comprising multiple positioning members 53, 54, 55 and 56.

Tapered closure structure 51 preferably comprises a porous or mesh-like structure constructed from a shape change metallic material that, in a delivery condition, provides a low profile, small diameter structure and expands during deployment to an enlarged, deployed condition in which it contacts a least a portion of the internal wall of the aneurysm. The porous or mesh-like structure may have generally large or small spaces between the structures and the spaces and structures may be symmetrical or asymmetrical and may be generally curved or generally linear and angular. Suitable types of expanding mesh-like structures are known and used, for example, in various types of stents. Tapered closure structure 51 may be covered or associated, at least in part, with a flexible fabric or membrane material that is biocompatible and biostable such as a silicone material, a PFTE material, Dacron™, or the like, or may be associated with other types of fibrous materials.

Tapered closure structure 51 may be joined to or associated with closure membrane 52 at a smaller diameter base portion 57. Closure structure 51 may have a perimeter that corresponds generally to the configuration of smaller diameter base portion 57 or, alternatively, the perimeter of closure structure 51 may have a larger or differently shaped configuration from that of smaller diameter base portion 57. In one embodiment, for example, closure structure 51 is mounted on or associated with a framework structure 58 in proximity to its perimeter and is mounted to or associated with base portion 57 at a location internal to its perimeter.

Positioning members 53, 54, 55 and 56 of closure device 50 may have a loop-like structure similar to the anchoring structures described above. Alternatively, positioning members 53, 54, 55 and 56 may comprise a solid metallic structure, a mesh-like discontinuous structure, or a structure in which a flexible material is mounted on or associated with framework structures defining the positioning members. Two or more positioning members may be provided and are arranged in a generally radially symmetrical arrangement with respect to closure structure 51. In another embodiment, a tapered, discontinuous mesh structure having a shallower configuration than that of tapered closure structure 51 may be provided as an anchoring structure.

Figure 4A:
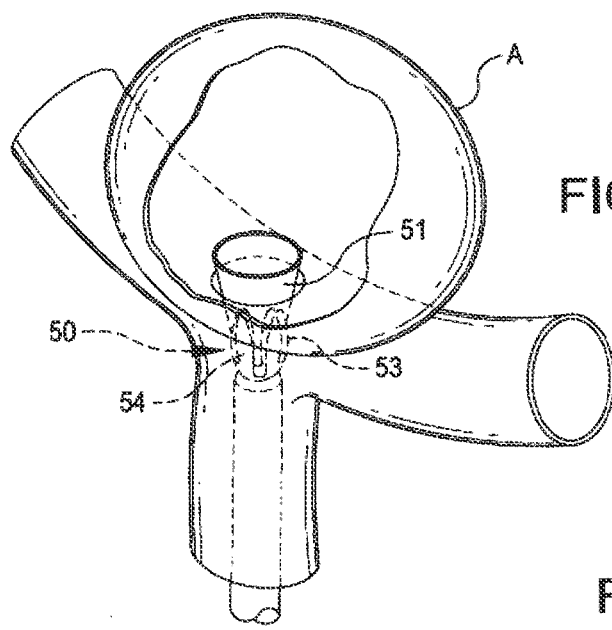
FIGS. 4A-4C schematically illustrate the implantable closure device of FIGS. 3A and 3B in partially and fully deployed conditions.
Figure 4B:
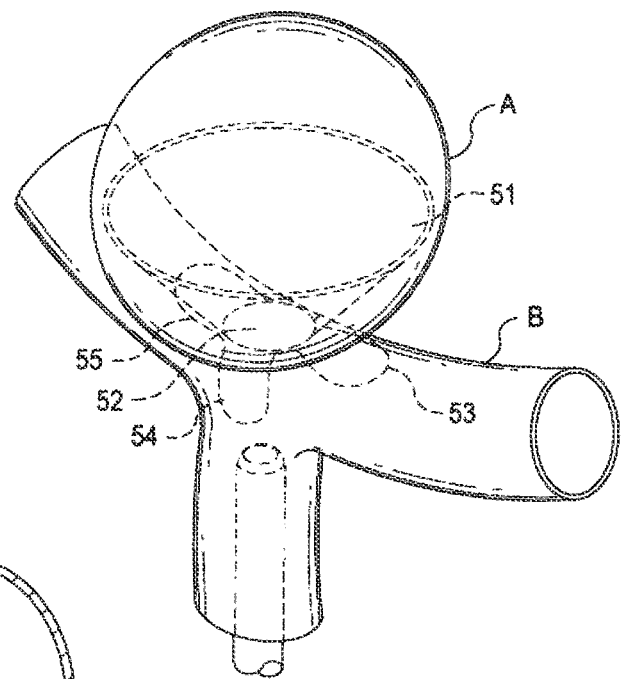
Figure 4C:
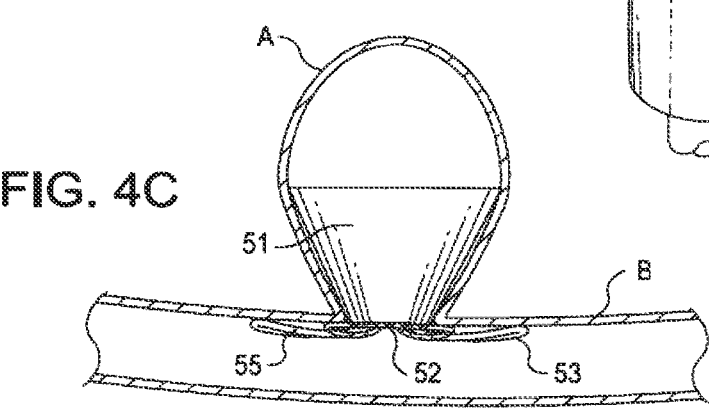

FIGS. 4A-4C illustrate the closure device 50 during deployment and in a deployed condition following deployment in and across an aneurysm. FIG. 4A illustrates closure device 50 partially inserted into an aneurysm A. Tapered closure structure 51 is deployed as a first anchoring structure through the aneurysm neck and positioned within the aneurysm with membrane 52 extending across and substantially closing the neck of the aneurysm. The positioning members 53, 54, 55 and 56 are deployed and reside outside the aneurysm neck following deployment and contact at least a portion of the blood vessel wall in proximity to the neck of the aneurysm. Placement of this closure system thus repairs the vessel wall and restores the vessel to a substantially normal and healthy configuration.

Figure 5:
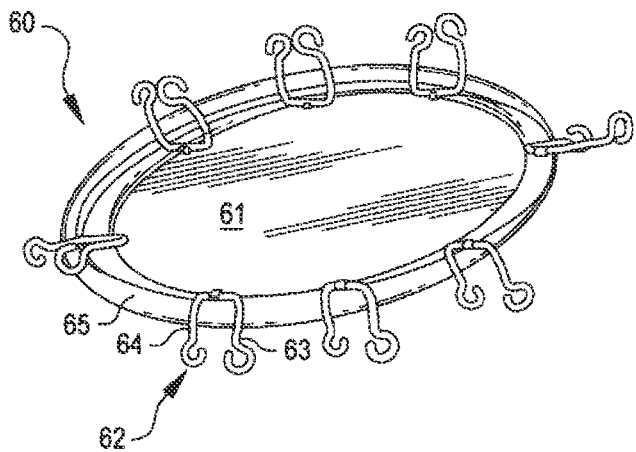
FIG. 5 illustrates a closure structure comprising a flexible patch having a plurality of anchoring structures provided near a perimeter of the closure structure.

FIG. 5 illustrates another embodiment of an implantable device 60 comprising a flexible closure structure 61 having a plurality of anchoring members 62 mounted on, or retained near, the periphery of the closure structure. Anchor members 62, as shown, have at least two spaced-apart arms 63, 64 and may be mounted at an interior or exterior surface of closure structure 61 or may alternatively be mounted through the closure structure, with opposing arms 63, 64 extending from opposite surfaces of closure structure 61. Arms 63, 64 may be located on closure structure such that a peripheral rim 65 of structure 61 is arranged outside the junction of opposing arms 63, 64 with closure structure 61.

Implantable device 60 is preferably radially foldable or compressible for minimally invasive delivery through catheter devices. In the delivery condition, arms 63, 64 may be in a substantially linear condition so that the device may be delivered in a small diameter, substantially cylindrical configuration. Following delivery of the device to the desired target site in a small diameter, delivery condition, one series of arms is deployed to its larger deployment condition and positioned on the interior of the aneurysm wall in proximity to the aneurysm neck. The other series of arms is deployed subsequently, causing both series of arms to assume their three-dimensional, spaced apart and generally opposed positions, with the second series of arms positioned on the internal blood vessel wall in proximity to the aneurysm neck. Closure structure 61 is positioned across the aneurysm neck to substantially cover the opening during deployment of the respective anchoring arms. Following placement of implantable device 60 across the neck of an aneurysm, closure structure 61 substantially covers the neck and arms 63, 64 provide anchoring points both inside the aneurysm and in the blood vessel. Peripheral rim 65, having a larger diameter cross section than that of closure structure 61, may provide additional coverage of the aneurysm neck and/or the vessel wall in proximity to the aneurysm neck.

FIGS. 6A-6D illustrate alternative closure devices. Closure system 70, shown in FIG. 6A, comprises a central closure structure 71 with a reinforced neck structure 72 and a plurality of anchoring structures 73 and 74. Closure structure 71 may optionally have an opening or slot provided in a generally central region. Reinforced neck structure 72 may be integral with closure structure 71 or constructed separately and mounted in proximity to a perimeter of closure structure 71. Neck structure 72 comprises a reinforcement member 75 and a flexible membrane member. In combination, the reinforced neck structure forms an upstanding collar structure that may be generally cylindrical, oval or the like, and is intended, following placement at the neck of an aneurysm, to project into the interior of the aneurysm and seal the neck region from the vessel. The reinforcement member 75 may be provided in a zig-zag pattern, as shown, or in another pattern in which it provides structural support for the upstanding neck structure. Although reinforced neck structure 72 is illustrated as projecting in a direction substantially orthogonal to the plane of closure structure 71, it will be appreciated that reinforced neck structure 72 may project in a direction that forms either an acute angle or an obtuse angle with respect to the plane of closure structure 71, depending on the desired application and the conformation of the body structure desired to be occluded.

Closure system 70 additionally comprises a skirt portion 76 extending from closure structure 71 or neck structure 72 and having a larger perimeter than either closure structure 71 or neck structure 72. The skirt portion acts to further seal boundaries of the opening desired to be occluded and is intended to remain on the outside of the opening—contacting, in the example of an aneurysm, the blood vessel wall in proximity to the neck of the aneurysm. Using a device incorporating a skirt portion is particularly desirable in applications where the geometry of the opening is irregular, and the dimensions of the skirt portion may be adjusted accordingly. The skirt portion preferably increases the deployed diameter of the occlusive device by at least about 10%, more preferably at least about 15% and, in some embodiments, at least about 20%. In yet other embodiments, the skirt portion preferably increases the deployed diameter of the occlusive device by at least about 30%.

Figure 6A:
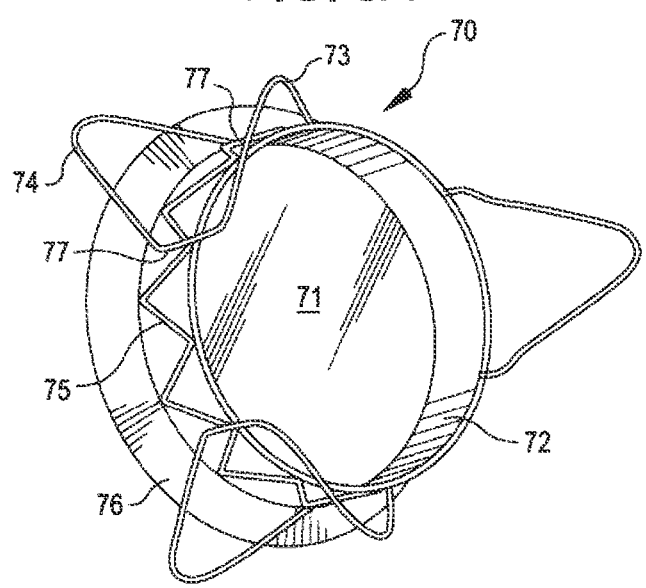
Figure 6B:
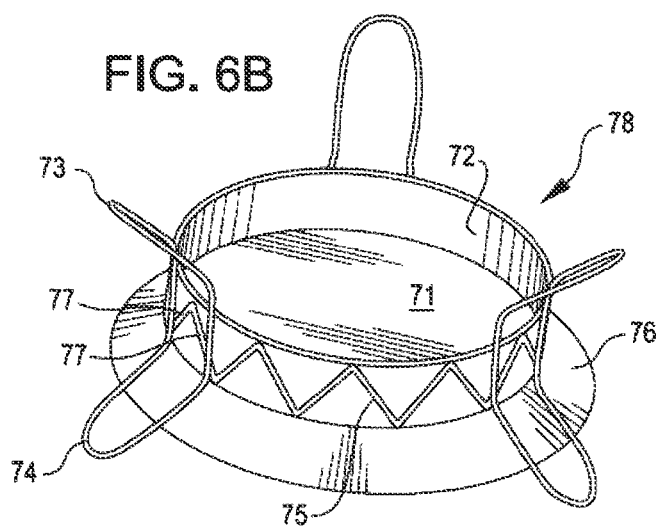

Anchoring structures 73, 74 are preferably constructed from a generally rigid material, preferably a shape memory material such as Nitinol. In the embodiment illustrated in FIG. 6A, anchoring structures 73 and 74 project on opposite sides of the plane of closure structure 71 and are joined by an intermediate structural support 77. The anchoring structures may be integral and provided as a single structure, or separate and oppositely positioned anchoring structures may be provided. Anchoring structures 73, 74 are illustrated in FIG. 6A as having a generally triangular configuration with rounded corners. In an alternative embodiment of closure device 78 shown in FIG. 6B, the anchoring structures have a more rounded, paperclip-like structure.

Anchoring structures may assume a variety of sizes and configurations and may have a generally broad or narrow profile. The anchoring structures may be substantially similar in size and configuration as illustrated or anchoring structures having different sizes and configurations may be provided. For some applications, anchoring structures may have a mesh-like or porous configuration. Although three sets of anchoring structures are illustrated, it will be appreciated that fewer or more anchoring structures may be provided and that the anchoring structures are generally arranged in a radially symmetrical arrangement with respect to the central patch.

FIG. 6C illustrates a similar closure system 80 comprising a central closure structure 81 having a generally cylindrical collar region 82 and flared skirt portion 83. The interface between collar region 82 and flared skirt portion 83 is generally curved and continuous. Reinforcement is provided by opposing anchoring arms 84, 85 which are staggered with respect to each other and arranged in a generally radially symmetrical pattern.

FIG. 6D illustrates a portion of another closure device 130 of the present invention in a partially deployed condition. Closure device 130 comprises first and second sets of anchoring structures 132 and 134 projecting from opposite sides of an intermediate collar structure 136 and generally transverse closure structure 138. Anchoring structures 132 and 134 are preferably constructed from a shape change material that forms a substantially cylindrical structure in the delivery condition and changes conformation during deployment to provide a larger diameter structure having anchoring structures 132, 134 forming a substantially circumferential, ring-like structure in the deployed or partially deployed condition, as shown in FIG. 6D. Anchoring structures 132, 134 may be substantially as illustrated in FIG. 6D in a deployed condition, or they may curve further toward a centerline of the device in a fully deployed condition, depending on the type and structure of the tissue defect being repaired by the implantable device. Similarly, intermediate collar structure 136 may have a substantially upstanding, cylindrical configuration in a fully deployed condition, as illustrated in FIG. 6D, or the intermediate collar structure may be angled or curved circumferentially outwardly, in combination with the anchoring structures, to provide a structure that contacts and firmly clamps the device to the tissue in proximity to the defect in an atraumatic manner. Various curved and/or bent device configurations in the deployed condition may be provided, depending on the size of the defect, the type and thickness of tissue being repaired, and the like.

Anchoring structures 132 and 134 are preferably substantially atraumatic and constructed to minimize trauma to tissue they contact in a deployed condition. In one embodiment, anchoring structures 132 and 134 have a generally cylindrical or tubular structure and cross-sectional configuration. In the partially deployed configuration illustrated in FIG. 6D, anchoring structures 132, 134 project on opposite sides of intermediate collar structure 136 and are arranged in a substantially aligned configuration, whereby upon deployment at a target site, opposing anchoring structures contact opposite tissue surfaces in proximity to a defect in substantially the same location. The distal terminal ends of anchoring structures 132, 134 form a generally large surface area, terminating in a generally blunt structure, to provide a substantially non-traumatic anchoring structure that contacts tissue to positively position and retain the closure structure across a defect without damaging the tissue it contacts.

While anchoring structures 132 and 134 are illustrated as generally triangular, wire structures having an overall length greater than the length of the intermediate collar structure, it will be appreciated that alternative configurations may be used. The anchoring structures may incorporate additional reinforcing or pressure distribution structures that may take the form of additional structures or surface areas. Alternatively or additionally, membranes such as those used for constructing the closure structure may be provided in connection with one or more anchoring structures.

One or more radiopaque markers are preferably provided in proximity to the ends of anchoring structures 132, 134 remote from intermediate collar structure, which correspond to the distal and proximal ends of the implantable device in a delivery condition. Radiopaque markers may be provided, for example, by associating a radiopaque material with a portion of the anchoring structure. Suitable radiopaque materials such as tantalum, gold, silver, barium, platinum, tungsten, and the like may be used. Radiopaque markers may be associated with an anchoring structure, for example, by gluing, adhering, crimping, welding, laser welding, or the like. Bands 133 and 135 may, for example, incorporate or comprise or be associated with radiopaque markers, thus marking the terminal ends of both sets of anchoring structures during and following deployment.

Intermediate collar structure 136 comprises reinforcing structure formed from ribs 137 that form a generally cylindrical reinforcing structure and are provided in a generally denser structure than that of anchoring structures 132, 134. Ribs 137 form a generally criss-crossing structure and may be bonded to, or associated with a membrane structure that is flexible and may be substantially coextensive with the collar structure. The collar structure may form a generally upstanding cylindrical structure in a deployed condition or, as described above, the collar structure and ribs may be angled or curved in an outward circumferential conformation. Transverse closure structure 138 may be mounted on or bonded to or formed with intermediate collar structure 136 and/or a membrane structure associated with the collar structure and may be substantially continuous or may be provided with a slot or opening for passage of a guidewire or another instrument. One or more radiopaque marker(s) is preferably associated with collar structure 136 and/or transverse closure structure 138.

Figure 7:
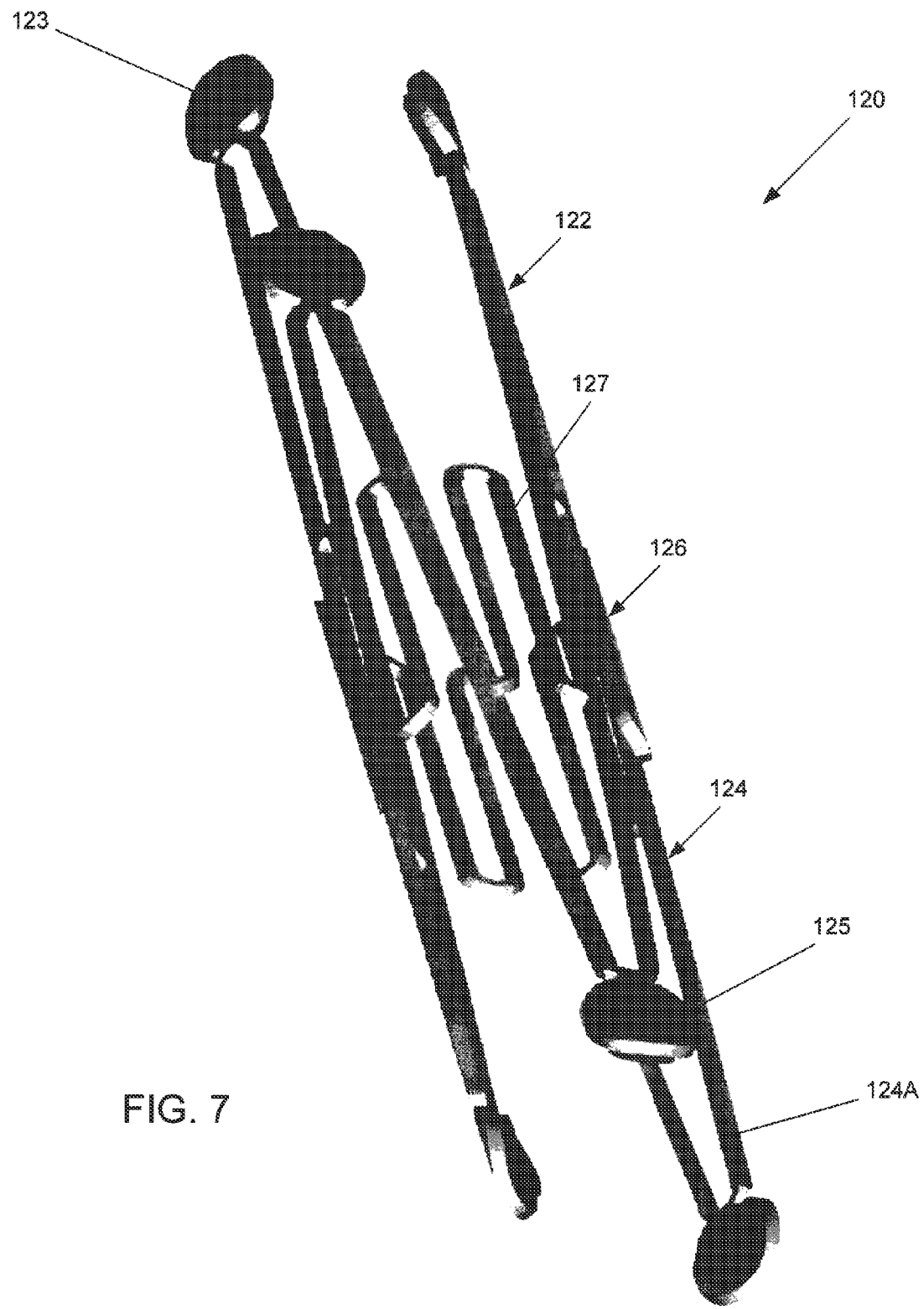
FIG. 7 illustrates an enlarged, schematic side view of another embodiment of an implantable device having a closure structure in combination with anchoring structures in a delivery condition.

FIG. 7 illustrates yet another embodiment of a closure device 120 of the present invention in a small diameter, delivery condition. Closure device 120 illustrated in FIG. 7, comprises first and second sets of anchoring structures 122 and 124 projecting from opposite sides of an intermediate collar structure 126 and generally transverse closure structure (not shown). Anchoring structures 122 and 124 preferably comprise a shape change material and form a substantially cylindrical structure in the delivery condition as shown in FIG. 7. These anchoring structures (122, 124) bend radially outwardly during deployment to form a substantially circumferential, ring-like structure in the deployed condition.

Anchoring structures 122 and 124 are preferably substantially atraumatic and constructed to minimize trauma to tissue they contact in a deployed condition. In one embodiment, anchoring structures 122 and 124 have a generally flattened structure and cross-sectional configuration. In the embodiment illustrated in FIG. 7, anchoring structures (122, 124) have substantially the same configuration, project on opposite sides of the intermediate collar structure, and are arranged in a substantially staggered or offset configuration. One of the anchoring structures, 124A, is longer than its neighboring structures. In alternative embodiments, anchoring structures 122 and 124 may vary in configuration and/or size, and may be arranged in a radically symmetrical or asymmetrical configuration. In the deployed condition, anchoring structures 122, 124 contact generally non-overlapping portions of tissue on opposite sides of the defect being closed. This arrangement is generally non-traumatic and promotes and preserves tissue viability and blood flow in areas contacted by the closure device. Enlarged distal and proximal pads, 123 and 125, respectively, may be associated with one or more anchoring structures 122 and 124, respectively, to promote positioning and deployment of the closure device and to provide a larger diameter contact footprint in areas of tissue contact.

While anchoring structures 122 and 124 are illustrated as generally triangular, flattened wire structures having an overall length greater than the length of the intermediate collar structure, it will be appreciated that alternative configurations may be used. The anchoring structures may incorporate additional reinforcing or pressure distribution structures that may take the form of additional structures or surface areas. Alternatively or additionally, membranes or mesh structures such as those used for constructing the closure structure may be provided in connection with one or more anchoring structures.

One or more radiopaque markers are preferably provided in proximity to the ends of anchoring structures 122, 124 remote from intermediate collar structure, which correspond to the distal and proximal ends of the implantable device in a delivery condition. Pads 123 and 125 may, for example, incorporate or comprise or be associated with radiopaque markers, thus marking the terminal ends of both sets of anchoring structures during and following deployment. Suitable radiopaque materials such as tantalum, gold, silver, barium, platinum, tungsten, and the like may be used. Discrete radiopaque markers may be associated with the anchoring structures, for example, by gluing, adhering, crimping, welding, laser welding, and the like.

Intermediate collar structure 126 comprises a generally cylindrical reinforcing structure formed from ribs 127 that form a generally cylindrical reinforcing structure and are provided in a generally denser structure than that of anchoring structures 122, 124. Ribs 127 are bonded to, or associated with a membrane structure (not shown) that is flexible and, in this embodiment, is substantially coextensive with the collar structure. The membrane structure may be associated with or formed integrally with a transverse closure structure (not shown). Radiopaque markers may additionally or alternatively be associated with collar structure 126 and/or the transverse closure structure.

FIG. 8 illustrates yet another embodiment of a closure device 90 in which an enlarged closure structure 91 provides an occluding surface in its central region and also provides the substrate for attachment of a reinforcing structure comprising a plurality of anchoring struts 92 and 93 that, in a deployed condition, form a petal-like loop pattern with opposed struts 92 and 93 being in a substantially mirror-image configuration. Struts 92, 93 are joined to one another by means of intermediate structures 94. The reinforcing structure may be formed as a single, interconnected structure or multiple independent structures may be connected, or mounted coordinately with one another.

As closure device 90 is deployed following delivery of the device, in a small diameter delivery condition to the neck of an opening, anchoring struts 92 are deployed first to the interior of the opening and positioned contacting or in proximity to the internal wall of the aneurysm, with intermediate structures 94 positioned generally at the neck of the opening. As deployment progresses, anchoring struts 93 are deployed and contact the internal vessel wall in proximity to the aneurysm opening, and the closure structure 91 is drawn against the opening from the direction of the vessel. In this embodiment, closure device 91 may be used to occlude openings having irregular conformations.

Figure 9:
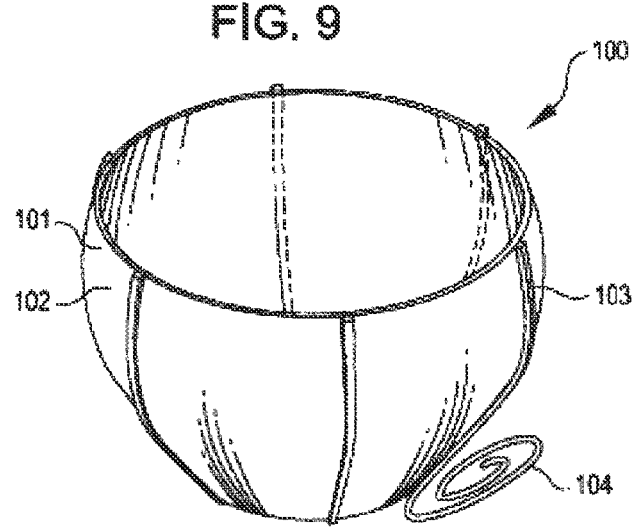
FIG. 9 illustrates an enlarged, schematic side perspective view of another embodiment of an implantable device having a generally bulbous occlusive member in a deployed condition.

FIG. 9 illustrates yet another embodiment of a closure device 100 in an expanded, deployed condition. Closure device 100 comprises a generally curved conical or bulbous structure 101, which may be formed, for example, from thin-film shape memory alloy, such as Nitinol. Curved structure 101 terminates at a small diameter end in a closure structure (not shown) and has an opening at the larger diameter end. In the embodiment illustrated in FIG. 8, curved structure 101 comprises a membrane wall 102 or a plurality of membrane panels reinforced by a plurality of ribs 103. Ribs 103 are generally arranged in a radially symmetrical pattern and fewer or more ribs may be provided. In another embodiment, membrane wall 102 may be reinforced by a mesh-like structure or another type of framework structure.

Closure device 100 additionally comprises at least one retaining structure 104 for positioning, and retaining device 100 across an opening. Retaining structure 104 may be in the form of a curved or coiled strip, or may be formed as a petal-like or loop-like structure, and multiple retaining structures 104 may be provided. During deployment of device 100, bulbous structure 101 is positioned for expansion inside the opening, while retaining structure(s) 104 remain outside the neck of the opening and anchor the device 100 within the opening by contacting the wall of the structure in proximity to the opening.

Figure 10:
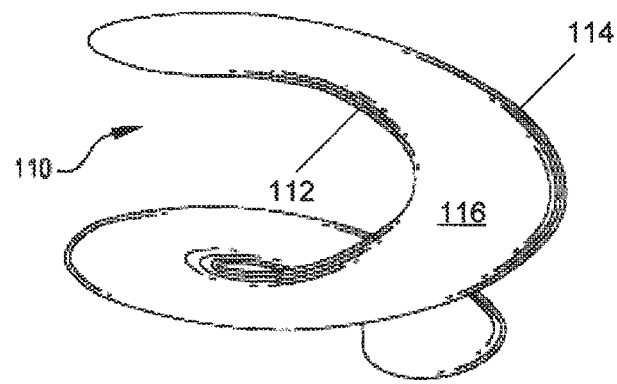
FIG. 10 illustrates an enlarged, schematic side perspective view of another embodiment of an implantable device having a coil structure in a deployed condition.

FIG. 10 illustrates yet another embodiment of a closure device 110 having a spiral configuration. A framework structure may be provided, for example, by reinforcing structures 112 and 114 provided at the internal and external boundaries of the spiral structure and a membrane 116 may be mounted to or formed integrally with the framework structure. In one embodiment, the spiral structure has a smaller diameter end and a larger diameter end. In another embodiment, a closure device of the present invention may comprise an opposed, dual spiral coil configuration. In this embodiment, an opposing coil structure comprising two coils joined in the middle at their small diameter portions and expanding radially in opposite directions (in an ascending/descending pattern) are provided.

A coil reinforcement structure may comprise Nitinol wire or a similar biocompatible, preferably shape change material, embedded or mounted to a membrane material that forms the closure structure. The membrane has dimensions such that overlapping loops of the membrane affixed to the coil reinforcement structure, when in a coiled configuration, form overlapping boundaries. Closure device 110 is deployed such that the terminal and larger diameter end of one of the coils is positioned inside the opening to be occluded and, as the device is deployed, the spiral shape forms and tightens against the opening. The small diameter portion of the device where the two opposing coil structures meet is positioned across the neck of the opening and the opposite coil is deployed into the region outside the opening and contacts the wall of the structure (such as a blood vessel) in proximity to the opening.

As outlined above, closure structures and membranes employed in the closure systems disclosed herein can be formed of a thin-film shape memory alloy, such as a thin-film Nitinol alloy. The thin-film Nitinol alloys employed in membranes and closure structures of the present invention preferably has a thickness of from about 0.5-100 microns, more preferably of from about 2-50 microns, and may be composed of between 45-55% each of titanium and nickel.

Thin-film Nitinol alloys may be prepared, for example, using sputtering techniques as described in U.S. Pat. No. 6,533,905, the disclosure of which is hereby incorporated by reference in its entirety. Such techniques may employ a mandrel, formed of steel, glass, silicon or the like, that has an exposed, etchable outer layer onto which is sputter-deposited a thin layer of a Nitinol alloy. Following sputter deposition, the thin layer of Nitinol alloy formed on the mandrel is heated under annealing conditions and the resulting thin-film is released from the mandrel, for example by exposing the mandrel and attached thin-layer to an etchant. Fenestrations, or small openings or pores, may be formed in the thin-film Nitinol alloy by forming a resist layer containing a pattern of openings on the annealed thin-film, exposing the coated thin-film to a solvent in order to create fenestrations corresponding to the pattern of openings, and removing the resist layer. Structural members may be positioned on the mandrel prior to sputter deposition of the Nitinol alloy, so that the thin-film is attached directly to the structural member.

The framework, or support members, and anchoring members employed in the closure devices may be cut or etched, for example, from a tube or cylinder of a thin-film shape memory alloy, such as a thin-film titanium-nickel alloys (e.g., Nitinol alloys). Techniques for etching thin-film shape memory alloys are well known in the art. In one embodiment, a thin-walled tube can be prepared, for example, as described by Gupta et al. (SMST-2003: Proc. Intl. Conf. Shape Memory Superelastic Technol., (Pacific Grove, Calif.) eds. A. R. Pelton & T. Duerig, p. 639, 2003). Briefly, multiple layers of think film Nitinol alloys and a sacrificial material (such as chromium) are sputter deposited sequentially onto a flat substrate surface, such as a polished and oxidized silicon wafer, with the first deposited layer being formed of chromium, and two subsequently deposited layers of Nitonol alloy being separated by a second layer of chromium. The Nitonol alloy layers may be from 1 to 40 microns in thickness, while the chromium layers may be approximately 500 Angstroms in thickness. Two photomask plates (referred to as Mask 1 and Mask 2) are employed, the masks having pre-determined pattern designs which determine the size and shape of the resulting structure, in this case a cylinder or tube. Mask 1 contains the design used to pattern the second chromium layer on the wafer and mask 2 contains a design to pattern the Nitonol alloy layers. Standard MEMS techniques are used to pattern the thin-film Nitonol alloy and chromium layers. Following deposition of the thin-film Nitonol alloy and chromium layers on the wafer, the multi-layered thin-film structure is removed from the wafer by immersing it in chromium etchant to dissolve all the chromium layers, creating a pocket between the first and second Nitonol alloy layers. The released thin-film structure, which has a generally rectangular shape, is transformed into a three-dimensional cylinder by inserting a close-fit mandrel formed, for example, from stainless steel, into the pocket between the two Nitonol alloy layers and heat treating the structure at 500° C. in a vacuum. Fenestration of any desired size, shape and pattern can be formed in the Nitonol alloy layer using standard photolithography techniques.

In another aspect, the implantable systems disclosed herein comprise a closure device having a device wire that, in combination with a detachment joint, detachably connects the implantable device to a delivery/pusher wire. A device wire is generally integral with or attached at its distal end to the implantable device through the detachment joint and employed to deliver the implantable device to the desired location in the body, generally by navigation through a guide catheter. Suitable device wires, detachment joints and delivery/pusher wires are well known in the art and may be used in association with closure devices of the present invention. Materials that may be employed for the device and delivery wires are well known in the art.

Closure systems of the present invention are used to repair defects in blood vessels such as aneurysms, and other physiological defects or cavities formed in lumens, tissue, and the like. Methods and systems of the present invention provide repair and reconstruction of a lumen wall or tissue defect using minimally invasive endoluminal techniques and without requiring invasive surgical procedures. The delivery and deployment procedures are generally straightforward and less time consuming than many alternative procedures and consequently reduce the risk of complications.

Figure 11:
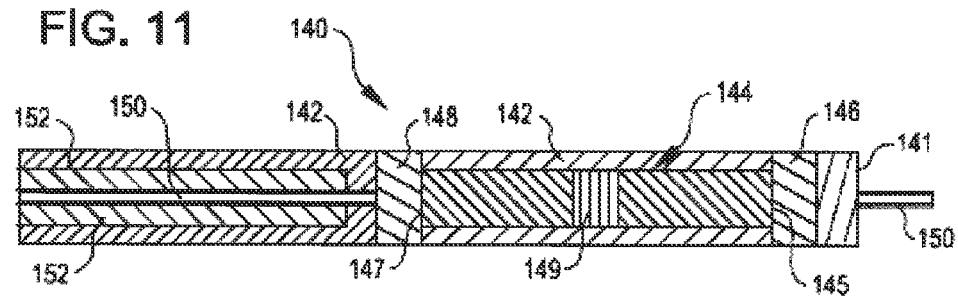
FIG. 11 illustrates an enlarged, schematic side view of an implantable device of the present invention in a delivery system.

FIG. 11 illustrates an implantable device of the present invention loaded in a delivery catheter for navigation to and deployment at a target repair site, and FIGS. 12A-E illustrate an exemplary delivery and deployment methodology. Delivery system 140 comprises a delivery catheter 142 having suitable dimensions, flexibility and pushability for navigation to a desired target repair site, such as an aneurysm or cavity formed in blood vessel. For embodiments in which delivery to the target delivery site, such as a neurovascular aneurysm, involves navigation through small lumen(s) and/or tortuous pathways, delivery catheter 142 may comprise a microcatheter having a small diameter and a generally high flexibility. Distal segment(s) of the delivery catheter may be more flexible, for example, than proximal sections. Numerous delivery catheters are known in the art and are suitable for use in delivery systems of the present invention.

Repair device 144, which may be any of the repair and/or occlusion devices described herein having two sets of opposed anchoring structures, is preferably preloaded in a small diameter, delivery condition, in a distal end 141 of delivery catheter 142. A distal end 145 of repair device 144, as it is positioned for delivery in delivery catheter 142, preferably corresponds to an anchoring structure intended for placement at the internal wall of an aneurysm or cavity to be repaired, or at a lumen wall or cavity surface that is opposite the internal wall relative to the delivery pathway. One or more radiopaque markers 146 may be provided at or near distal end 145 of repair device 144. Proximal end 147 of repair device 144, as it is positioned for delivery in delivery catheter 142, preferably corresponds to an anchoring structure intended for placement at a vessel wall near the neck of an aneurysm or cavity to be repaired, or at an inner lumen wall or cavity surface relative to the delivery pathway. One or more radiopaque markers 148 may be provided at or near proximal end 147 of repair device 144. Repair device 144 may additionally or alternatively incorporate a radiopaque marker in proximity to a central portion of the device, corresponding generally to a closure structure 149 of the device. Radiopaque markers may additionally or alternatively be provided in association with delivery catheter 142, marking locations corresponding to the distal and proximal portions of repair device 144, respectively.

The delivery system illustrated in FIGS. 11 and 12A-E employs a guidewire 150 for guidance and positioning of repair device 144 and a pusher 152 having a guidewire lumen and positioned for contacting a proximal portion 147 of repair device 144 and moving it in relation to delivery catheter 142. Suitable guidewires and pushers are well known in the art and may be used for delivery of repair and occlusion devices of the present invention.

Figure 12A:
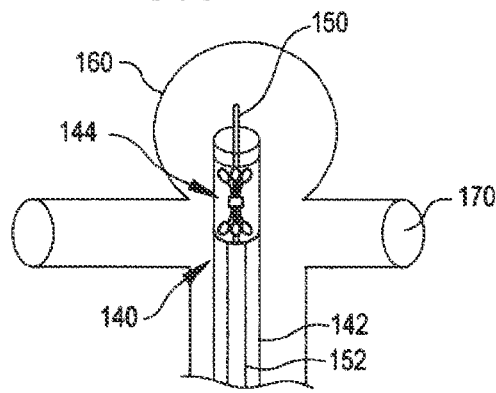
FIGS. 12A-E illustrate an enlarged, schematic view of a deployment methodology useful for placing devices of the present invention.
Figure 12B:
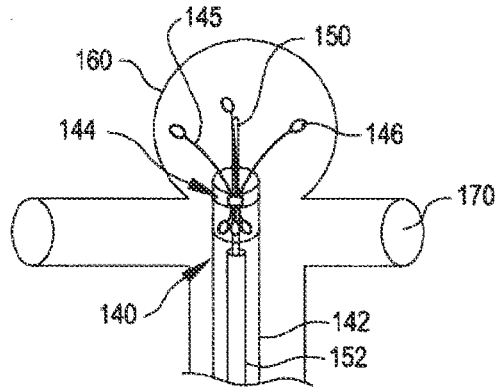

Methods for repairing a physiological defect or closing an opening or cavity 160 thus involve navigating a repair device 144 in a small diameter, delivery condition to a target repair site over a guidewire 150 using non-invasive or minimally invasive techniques and positioning a distal end of the repair device 144, corresponding to a first anchoring structure 145, at or in the opening to be repaired, as illustrated in FIG. 12A. Alternatively, repair device 144 may be positioned by positioning a radiopaque marker associated with an intermediate collar or closure structure 149 across the opening of the aneurysm or defect 160 in blood vessel 170. The first anchoring structure, which generally comprises a series of anchoring arms 145, is then deployed by pushing the distal end of the repair device 144 out of the delivery catheter 142 and/or withdrawing the delivery catheter 142 to position the first set of anchoring structures in proximity to or contacting the internal aneurysm wall in proximity to the neck, as shown in FIG. 12B. Upon deployment, the first set of anchoring arms 145 expands and unfolds circumferentially, with the anchoring structures positioned contacting or in proximity to a surface of the defect opposite, or on the other side of, the defect being repaired from the perspective of the delivery pathway. Radiopaque markers 146 provided on the first anchoring structure may be monitored, during deployment and positioning, to assure correct and atraumatic positioning.

Figure 12C:
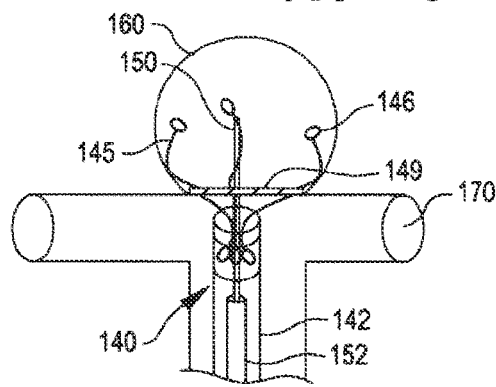
Figure 12D:
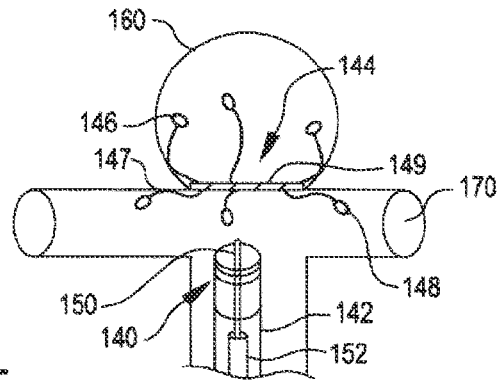
Figure 12E:
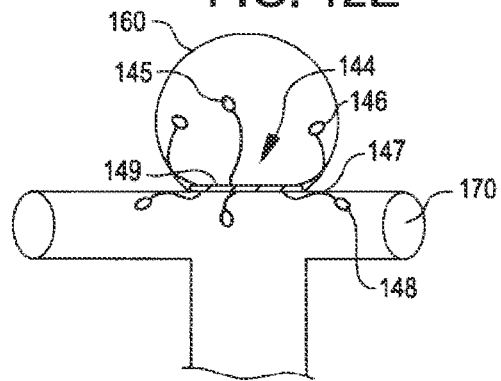

Following deployment of the first anchoring structure, an intermediate portion of the repair device comprising the closure structure 149 is deployed generally across the opening to be repaired and occludes the defect opening, as shown in FIG. 12C. Upon deployment of the intermediate closure structure 149, the closure structure unfolds or expands to substantially cover the opening. In this condition, the first set of anchoring arms 145 contacts or is in close proximity to one side of the internal wall of the aneurysm in proximity to the opening and the closure structure 149 covers the cavity opening. The proximal section of the repair device, comprising a second anchoring structure 147 and associated radiopaque markers 148 is then deployed, as shown in FIG. 12D, by pushing out of the delivery catheter 142 or withdrawing the catheter in relationship to the closure device. Upon deployment of the second anchoring structure, its anchoring arms 147 expand and unfold outwardly and are positioned contacting or in proximity to a surface of the defect bordering or forming part of the delivery pathway. At this point, the closure device 144 is securely deployed and the guidewire 150 is withdrawn into the delivery catheter 142. The delivery system 140 is withdrawn from the site and the closure device effectively repairs the opening, as shown in FIG. 12E.

Methods and systems of the present invention thus effectively repair an anatomical defect or opening by mounting a closure structure to substantially cover the opening and supporting and retaining the closure structure in position across the opening with anchoring structures positioned on both opposed surfaces of the lumen or tissue in proximity to the defect. Subsequent regrowth of cells and re-endothelialization of tissue in the area of the device placement effectively restores tissue function and effectively repairs the defect. Radiopaque markers are preferably used to deploy and position the device and may be used to monitor the position of the device at various times following placement.

While in the foregoing specification this invention has been described in relation to certain preferred embodiments thereof, and many details have been set forth for purposes of illustration, it will be apparent to those skilled in the art that the invention is susceptible to various changes and modifications as well as additional embodiments, and that certain of the details described herein may be varied considerably without departing from the basic spirit and scope of the invention.

All of the patent references and publications cited in this specification are incorporated by reference herein in their entireties.

We claim:

1. An implantable device for repairing an opening or cavity in a target tissue defect, the implantable device being adjustable from a delivery condition in which it assumes a generally small diameter configuration to a deployed condition in which it assumes a larger diameter configuration, the implantable device comprising:
    a closure structure sized to substantially cover the opening or cavity when the device is in the deployed condition;
    a collar structure provided in proximity to a perimeter of the closure structure, the collar structure configured to engage at least a portion of tissue at the opening or cavity when the device is in the deployed condition;
    a first anchoring structure extending in a first direction from a plane defined by the closure structure when the device is in the deployed condition; and
    a second anchoring structure extending in a generally opposite second direction from the plane defined by the closure structure when the device is in the deployed condition,
    wherein the first anchoring structure extending in the first direction faces generally toward the tissue defect and the second anchoring structure extending in the second direction faces generally away from the tissue defect,
    wherein the first and second anchoring structures are integrally formed and comprise a generally atraumatic, single looped structure extending beyond a periphery of the collar structure when the device is in the deployed condition.

2. The implantable device of claim 1, further comprising at least one radiopaque marker associated with at least one of the first and second anchoring structures.

3. The implantable device of claim 1 wherein the closure structure has a substantially continuous occlusive surface area.

4. The implantable device of claim 1 wherein the closure structure has at least one opening to facilitate passage of another device.

5. The implantable device of claim 1 wherein the closure structure comprises a material selected from the group consisting of: silicone materials; rubber materials; woven and non-woven fabrics; fluoropolymer compositions; polymeric materials, polyurethane materials, metallic materials and combinations thereof.

6. The implantable device of claim 1 wherein the closure structure comprises a thin film shape memory alloy.

7. The implantable device of claim 1 wherein the closure structure has a porous surface structure provided over at least a portion of its surface area.

8. The implantable device of claim 1 wherein the closure structure comprises a material that is permeable to liquids but substantially excludes cells from traversing the closure structure.

9. The implantable device of claim 1 wherein the collar structure is generally cylindrical and extends in a plane generally orthogonal to that of the closure structure when the device is in the deployed condition.

10. The implantable device of claim 1 wherein the first and second anchoring structures have a material density over their surface area that is less than the density of the closure structure over its surface area.

11. The implantable device of claim 1 wherein the first and second anchoring structures comprise a biocompatible shape memory alloy material.

12. The implantable device of claim 1 wherein the first and second anchoring structures have substantially the same configurations and/or dimensions.

13. The implantable device of claim 1 wherein the first and second anchoring structures are substantially aligned with one another in the deployed condition.

14. The implantable device of claim 1 wherein the implantable device further comprises one or more of the following: agents that promote cellular ingrowth and attachment at the target site; hydrophilic agents; hydrophobic agents; bonding agents; friction-reducing agents; radiopaque agents; antibioticagents; thrombogenic agents; anti-thrombogenic agents; therapeutic agents; hydrogel compositions; anti-inflammatory agents; anti-restenosis agents; radioactive agents; and combinations thereof.

15. A device for treating a tissue defect in a physiological lumen of a human subject, wherein the device is selectively transformable between a low profile delivery configuration and a deployed configuration sized to fit within the opening of the tissue defect, and wherein, in the deployed configuration, the device comprises:
    a closure system configured to repair and/or occlude an opening of the tissue defect in the physiological lumen, the closure system including—
        a radially expandable collar structure configured to engage tissue on or proximate the opening;
        a closure structure coupled to the collar structure and positioned within the collar structure, wherein the closure structure is sized to substantially cover the opening; and
        expandable atraumatic anchoring structures distributed around a circumference of the collar structure and configured to engage tissue above and below the opening,
    wherein the expandable atraumatic anchoring structures include at least a first anchoring structure extending in a first direction from a plane defined by the closure structure and a second anchoring structure extending in a second, opposite direction from the plane defined by the closure structure, wherein the first and second anchoring structures are integrally formed and comprise a single looped structure, and
    wherein the first anchoring structure is positioned to engage tissue in a cavity of the tissue defect and above the opening, and the second anchoring structure opposite the first anchoring structure is positioned to engage tissue outside the cavity and below the opening.

16. The device of claim 15 wherein the closure system further comprises a skirt portion extending from the collar structure and toward tissue on or proximate the opening, the skirt portion configured to provide a seal between the device and the tissue on or proximate the opening.

17. The device of claim 16 wherein the skirt portion has a flared, curved shape when the device is in the deployed configuration.

18. The device of claim 16 wherein, when the device is in the deployed configuration, the collar structure has a first diameter and the skirt portion has a second diameter greater than the first diameter.

19. The device of claim 18 wherein the second diameter is 10% greater than the first diameter in the deployed configuration.

20. The device of claim 18 wherein the second diameter is 20% greater than the first diameter in the deployed configuration.

21. The device of claim 15 wherein the tissue defect an aneurysm in a blood vessel of the human subject, and wherein the device is configured to occlude the aneurysm from the blood vessel.

22. The device of claim 15 wherein the first and second anchoring structures are coupled by an intermediate structural support and are configured to receive tissue at the opening therebetween.

23. The device of claim 15 wherein the radially expandable collar structure is generally cylindrical and the closure structure extends in a plane generally orthogonal to that of the collar structure when the device in the deployed configuration.

24. The device of claim 15 wherein the expandable anchoring structures are configured to engage non-overlapping portions of tissue above and below the opening.

25. An implantable device configured for placement at an opening of a physiological cavity, the implantable device comprising:
    a neck structure having an outer surface configured to be positioned in proximity to the opening of the physiological cavity;
    a plurality of anchoring structures including at least a first anchoring structure projecting from the neck structure in a first direction toward the cavity and a second anchoring structure integrally formed with the first anchoring structure projecting from the neck structure in a second direction opposite the first direction and away from the cavity, wherein the first and second anchoring structures are integrally formed and comprise a generally atraumatic, single looped structure; and
    a closure structure positioned within an interior of the neck structure, the closure structure configured to occlude the opening,
    wherein the implantable device is selectively transformable between a delivery condition and a deployed condition sized to fit within the opening of the physiological cavity.

26. The implantable device of claim 25 wherein the neck structure is generally cylindrical and configured to radially expand to engage tissue at or in proximity to the opening with the outer surface when in the deployed condition.

27. The implantable device of claim 25 wherein a perimeter of the first and/or second anchoring structure defines a generally triangular configuration with an atraumatic terminal end when the implantable device is in the deployed condition.

28. The implantable device of claim 25, further comprising a skirt portion extending from the neck structure and configured to engage tissue outside of the physiological cavity to further occlude the opening when the implantable device is in the deployed condition.

29. The implantable device of claim 28 wherein, in the deployed condition, the neck structure radially expands to a first cross-sectional dimension and the skirt portion radially expands to a second cross-sectional dimension greater than the first cross-sectional dimension.

* * * * *

UNITED STATES PATENT AND TRADEMARK OFFICE
CERTIFICATE OF CORRECTION

PATENT NO. : 9,510,835 B2
APPLICATION NO. : 14/022088
DATED : December 6, 2016
INVENTOR(S) : Eskridge et al.

It is certified that error appears in the above-identified patent and that said Letters Patent is hereby corrected as shown below:

On the Title Page

Item (72), in Column 1, in "Inventors", Line 5, delete "Freemont," and insert -- Fremont, --, therefor.

Item (56), in Column 2, under "Other Publications", Line 1, delete "Polytetraflouroethylene" and insert -- Polytetrafluoroethylene --, therefor.

On the page 4, in Column 2, under "Other Publications", Line 10, delete ""Concourse" and insert -- "Concours --, therefor.

In the Specification

In Column 17, Line 25, before "45," insert -- and --.

Signed and Sealed this
Seventh Day of March, 2017

Michelle K. Lee
*Director of the United States Patent and Trademark Office*